(12) United States Patent
Evans et al.

(10) Patent No.: US 10,004,854 B2
(45) Date of Patent: Jun. 26, 2018

(54) LOW RADIAL PROFILE NEEDLE SAFETY DEVICE

(71) Applicant: West Pharmaceutical Services, Inc., Exton, PA (US)

(72) Inventors: Christopher Evans, Long Valley, NJ (US); Brian Costello, Whitehouse Station, NJ (US); Christopher Gieda, Long Valley, NJ (US); Raymond Protasiewicz, Whippany, NJ (US); Kristofer Meehan, Broomfield, CO (US)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 310 days.

(21) Appl. No.: 14/702,914

(22) Filed: May 4, 2015

(65) Prior Publication Data

US 2015/0246182 A1    Sep. 3, 2015

Related U.S. Application Data

(63) Continuation-in-part of application No. 14/383,364, filed as application No. PCT/US2013/029518 on Mar. 7, 2013.

(Continued)

(51) Int. Cl.
*A61M 5/32* (2006.01)

(52) U.S. Cl.
CPC .......... *A61M 5/3272* (2013.01); *A61M 5/326* (2013.01); *A61M 5/3204* (2013.01); *A61M 2005/3267* (2013.01)

(58) Field of Classification Search
CPC .................................................. A61M 5/326
See application file for complete search history.

(56) References Cited

U.S. PATENT DOCUMENTS 4,425,120 A * 1/1984 Sampson ............ A61M 5/3271
604/198
4,731,059 A   3/1988 Wanderer et al.
(Continued)

FOREIGN PATENT DOCUMENTS

FR      2884723 A1   10/2006
JP   2014-059019 A    4/2014
(Continued)

OTHER PUBLICATIONS

Office Action dated Apr. 17, 2017 in U.S. Appl. No. 14/383,364 by Evans.
(Continued)

*Primary Examiner* — Bhisma Mehta
*Assistant Examiner* — Matthew A Engel
(74) *Attorney, Agent, or Firm* — Panitch Schwarze Belisario & Nadel LLP

(57) ABSTRACT

A needle safety device has an outer tube within which a syringe barrel from which a cannula extends is slideably receivable. A collar in the outer tube is moveable relative thereto and rotatably attachable to the distal end of the barrel. A force member biases the outer tube in a distal direction. A cannula shield able to receive the cannula therein is in the outer tube. The cannula shield is fixedly attached to a cap removably attached to the outer tube. A track is formed in the inner surface of the outer tube. A pin extending radially outwardly from the collar slidingly engages the track. In a pre-injection position, the cannula is entirely within the outer tube. In a full-insertion position, the cannula extends beyond the outer tube. In a locked position, the cannula is irreversibly retained entirely within the outer tube.

7 Claims, 17 Drawing Sheets

Related U.S. Application Data

(60) Provisional application No. 61/607,711, filed on Mar. 7, 2012.

(56) References Cited

U.S. PATENT DOCUMENTS

| | | | |
|---|---|---|---|
| 4,865,591 A * | 9/1989 | Sams | A61M 5/31553 222/287 |
| 4,894,055 A * | 1/1990 | Sudnak | A61M 5/3271 604/110 |
| 4,900,311 A * | 2/1990 | Stern | A61M 5/3271 604/198 |
| 4,917,673 A | 4/1990 | Coplin | |
| 4,923,446 A * | 5/1990 | Page | A61M 5/3243 604/198 |
| 4,966,592 A | 10/1990 | Bums et al. | |
| 5,242,401 A | 9/1993 | Colsky | |
| 5,267,972 A | 12/1993 | Anderson | |
| 5,312,347 A | 5/1994 | Osborne et al. | |
| 5,346,480 A * | 9/1994 | Hess | A61M 5/3271 604/197 |
| 5,389,085 A * | 2/1995 | D'Alessio | A61M 5/3271 604/198 |
| 5,472,430 A | 12/1995 | Vaillancourt et al. | |
| 5,569,190 A * | 10/1996 | D'Antonio | A61D 7/00 604/135 |
| 5,573,513 A | 11/1996 | Wozencroft | |
| 5,591,138 A * | 1/1997 | Vaillancourt | A61M 5/3271 604/192 |
| 5,595,566 A * | 1/1997 | Vallelunga | A61M 5/3243 604/110 |
| 5,624,402 A | 4/1997 | Imbert | |
| 5,688,241 A | 11/1997 | Asbaghi | |
| 5,785,691 A | 7/1998 | Vetter et al. | |
| 6,017,329 A | 1/2000 | Hake | |
| 6,027,482 A | 2/2000 | Imbert | |
| D430,293 S | 8/2000 | Jansen | |
| D431,864 S | 10/2000 | Jansen | |
| 6,183,446 B1 | 2/2001 | Jeanbourquin | |
| 6,190,364 B1 | 2/2001 | Imbert | |
| 6,196,998 B1 | 3/2001 | Jansen et al. | |
| 6,280,418 B1 | 8/2001 | Reinhard et al. | |
| D447,797 S | 9/2001 | Odell et al. | |
| D457,954 S | 5/2002 | Wallace et al. | |
| D461,244 S | 8/2002 | Niermann | |
| 6,432,088 B1 | 8/2002 | Huang et al. | |
| D468,016 S | 12/2002 | Mosler et al. | |
| 6,491,665 B1 | 12/2002 | Vetter et al. | |
| 6,491,667 B1 | 12/2002 | Keane et al. | |
| 6,520,935 B1 | 2/2003 | Jansen et al. | |
| 6,524,282 B1 | 2/2003 | Sudo et al. | |
| 6,547,764 B2 | 4/2003 | Larsen et al. | |
| 6,569,124 B1 | 5/2003 | Perouse | |
| 6,632,199 B1 | 10/2003 | Tucker et al. | |
| 6,648,858 B2 | 11/2003 | Asbaghi | |
| 6,776,777 B2 | 8/2004 | Barrelle | |
| 6,821,267 B2 | 11/2004 | Veillon, Jr. et al. | |
| 6,855,129 B2 | 2/2005 | Jensen et al. | |
| 6,884,237 B2 * | 4/2005 | Asbaghi | A61M 5/3272 604/192 |
| 6,926,697 B2 | 8/2005 | Malenchek | |
| 6,986,760 B2 | 1/2006 | Giambattista et al. | |
| 7,241,278 B2 * | 7/2007 | Moller | A61M 5/24 604/211 |
| 7,314,464 B2 | 1/2008 | Giambattista et al. | |
| 7,374,555 B2 | 5/2008 | Heinz et al. | |
| D570,478 S | 6/2008 | Sudo | |
| D581,046 S | 11/2008 | Sudo | |
| D581,049 S | 11/2008 | Sudo | |
| 7,462,168 B2 | 12/2008 | Stonehouse et al. | |
| D589,612 S | 3/2009 | Sudo | |
| 7,497,847 B2 | 3/2009 | Crawford et al. | |
| D596,290 S | 7/2009 | Kawamura | |
| 7,648,481 B2 | 1/2010 | Geiger et al. | |
| 7,666,164 B2 | 2/2010 | Giambattista et al. | |
| 7,699,813 B2 | 4/2010 | Liversidge | |
| 7,806,861 B2 | 10/2010 | Witowski | |
| 7,828,777 B2 | 11/2010 | Vetter et al. | |
| RE42,355 E | 5/2011 | Heiniger | |
| 8,016,797 B2 | 9/2011 | Gratwohl et al. | |
| 8,052,653 B2 | 11/2011 | Gratwohl et al. | |
| 8,062,252 B2 | 11/2011 | Alheidt et al. | |
| 8,062,265 B2 | 11/2011 | Millerd | |
| 8,075,522 B2 | 12/2011 | Larsen et al. | |
| 8,128,594 B1 | 3/2012 | Chang | |
| 8,287,501 B2 | 10/2012 | Wei | |
| 8,303,541 B2 | 11/2012 | Chun | |
| 8,328,765 B2 | 12/2012 | Daily et al. | |
| 9,067,024 B2 | 6/2015 | Roberts et al. | |
| 9,192,731 B2 * | 11/2015 | Roberts | A61M 5/326 |
| 9,272,098 B2 * | 3/2016 | Hourmand | A61M 5/2033 |
| 2001/0003150 A1 | 6/2001 | Imbert | |
| 2001/0031949 A1 * | 10/2001 | Asbaghi | A61M 5/326 604/198 |
| 2002/0004652 A1 * | 1/2002 | Asbaghi | A61M 5/326 604/242 |
| 2002/0133122 A1 | 9/2002 | Giambattista et al. | |
| 2003/0050609 A1 * | 3/2003 | Sams | A61M 5/20 604/208 |
| 2003/0120209 A1 | 6/2003 | Jensen et al. | |
| 2003/0144630 A1 * | 7/2003 | Chang | A61M 5/3272 604/198 |
| 2004/0111064 A1 * | 6/2004 | Asbaghi | A61M 5/3272 604/198 |
| 2004/0215148 A1 | 10/2004 | Hwang et al. | |
| 2005/0075611 A1 | 4/2005 | Hetzler et al. | |
| 2005/0107740 A1 | 5/2005 | Jensen et al. | |
| 2005/0113750 A1 | 5/2005 | Targell | |
| 2006/0189933 A1 * | 8/2006 | Alheidt | A61M 5/326 604/110 |
| 2008/0262436 A1 * | 10/2008 | Olson | A61M 5/2033 604/198 |
| 2009/0005742 A1 * | 1/2009 | Liversidge | A61M 5/326 604/263 |
| 2009/0024093 A1 * | 1/2009 | Carrel | A61M 5/326 604/198 |
| 2009/0149816 A1 | 6/2009 | Hetzler et al. | |
| 2010/0094207 A1 * | 4/2010 | Boyd | A61M 5/31555 604/68 |
| 2010/0198163 A1 | 8/2010 | Bonnet | |
| 2010/0262083 A1 | 10/2010 | Grunhut et al. | |
| 2010/0268170 A1 | 10/2010 | Carrel et al. | |
| 2010/0286623 A1 * | 11/2010 | Liversidge | A61M 5/326 604/198 |
| 2010/0298779 A1 | 11/2010 | Hetzler et al. | |
| 2011/0015578 A1 | 1/2011 | Lowke | |
| 2011/0046563 A1 | 2/2011 | Vetter et al. | |
| 2011/0054411 A1 | 3/2011 | Dowds et al. | |
| 2011/0112486 A1 | 5/2011 | Gnrnard | |
| 2011/0118667 A1 * | 5/2011 | Zaiken | A61M 5/3202 604/138 |
| 2011/0137261 A1 | 6/2011 | Garber et al. | |
| 2011/0319832 A1 * | 12/2011 | Chun | A61M 5/326 604/198 |
| 2011/0319833 A1 | 12/2011 | Chun | |
| 2012/0041368 A1 | 2/2012 | Karlsson | |
| 2012/0253289 A1 | 10/2012 | Cleathero | |
| 2012/0277724 A1 | 11/2012 | Larsen et al. | |
| 2012/0310206 A1 * | 12/2012 | Kouyoumjian | A61M 5/31525 604/506 |
| 2012/0316508 A1 | 12/2012 | Kirchhofer | |
| 2012/0323186 A1 | 12/2012 | Karlsen et al. | |
| 2013/0204186 A1 | 8/2013 | Moore et al. | |
| 2013/0211338 A1 * | 8/2013 | Roberts | A61M 5/326 604/198 |
| 2013/0261558 A1 * | 10/2013 | Hourmand | A61M 5/2033 604/197 |
| 2013/0324923 A1 | 12/2013 | Roberts et al. | |
| 2014/0012208 A1 * | 1/2014 | Plumptre | A61M 5/31543 604/211 |
| 2015/0018773 A1 * | 1/2015 | Evans | A61M 5/3272 604/198 |

(56) References Cited

U.S. PATENT DOCUMENTS

FOREIGN PATENT DOCUMENTS

| WO | 9014112 A1 | 11/1990 |
| WO | 2009137845 A1 | 11/2009 |
| WO | 2015022787 A1 | 2/2015 |

OTHER PUBLICATIONS

Int'l Search Report and Written Opinion dated Jun. 24, 2013 in Int'l Application No. PCT/US2013/029518.

* cited by examiner

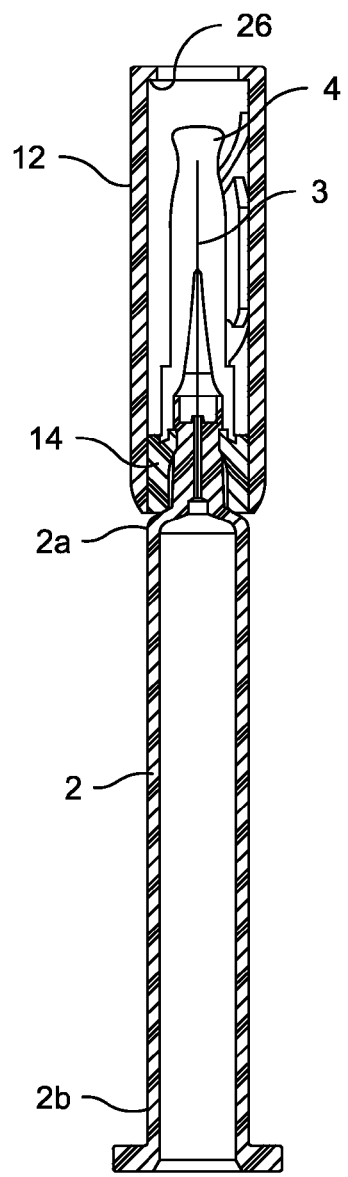
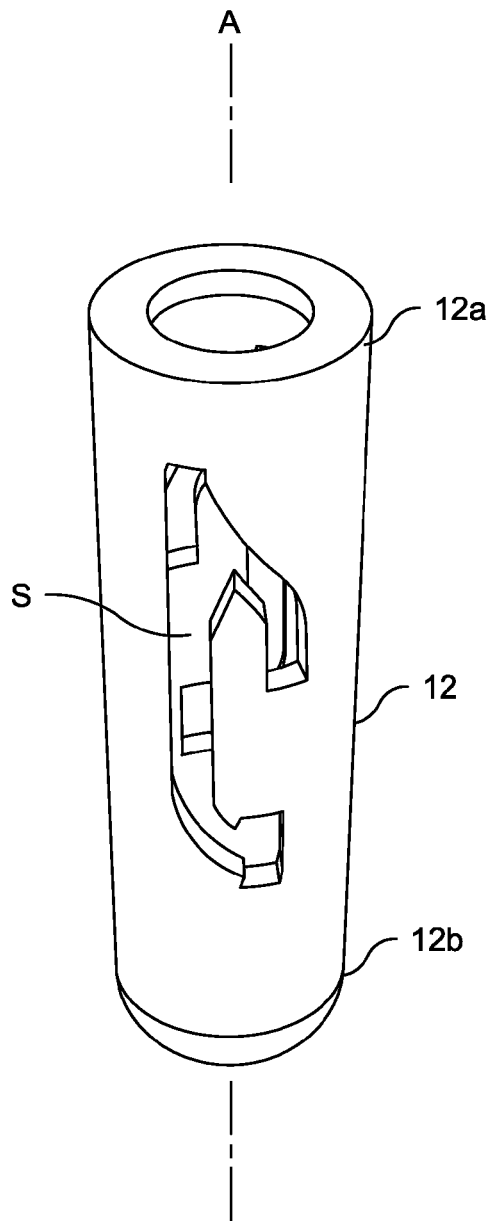
Fig. 3
Fig. 4

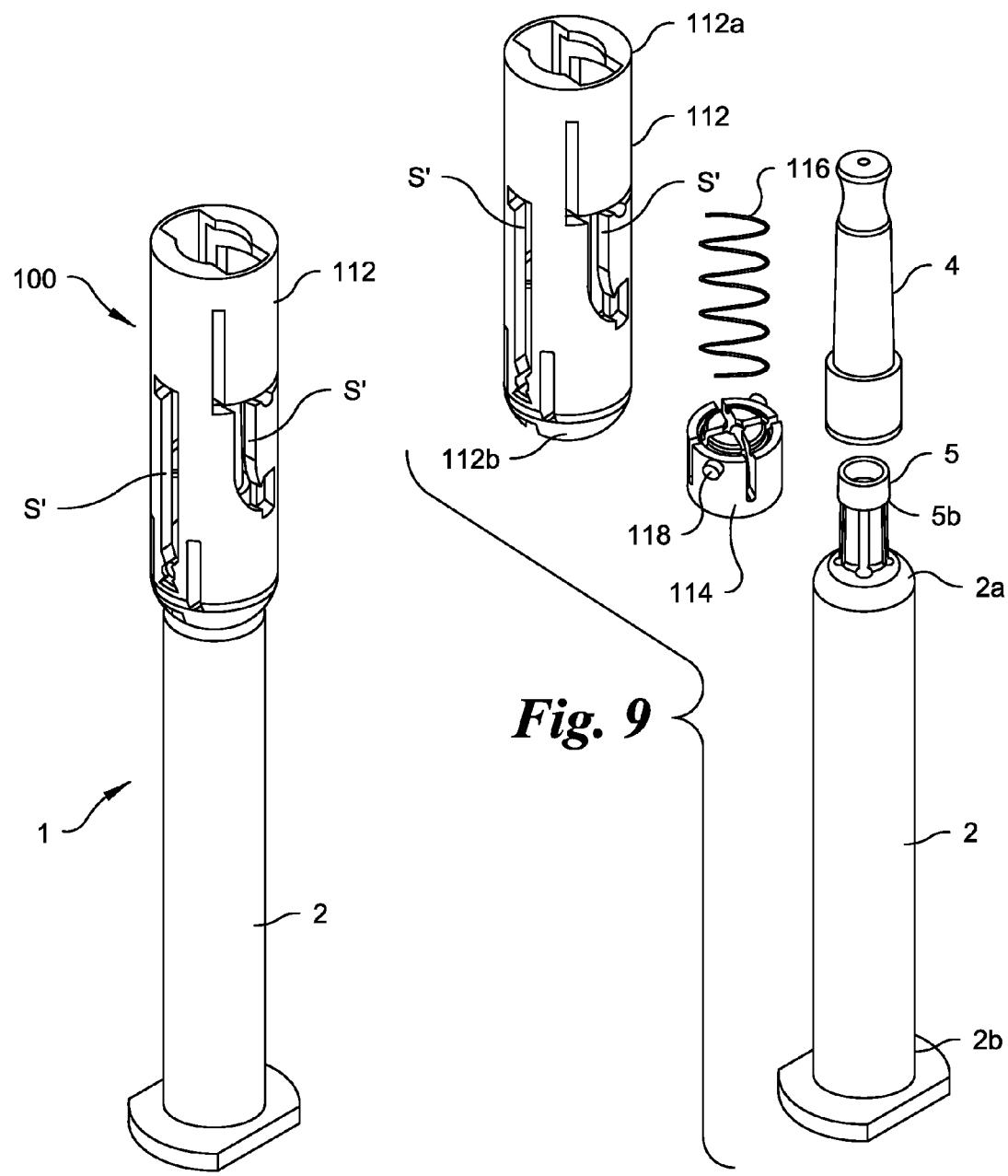

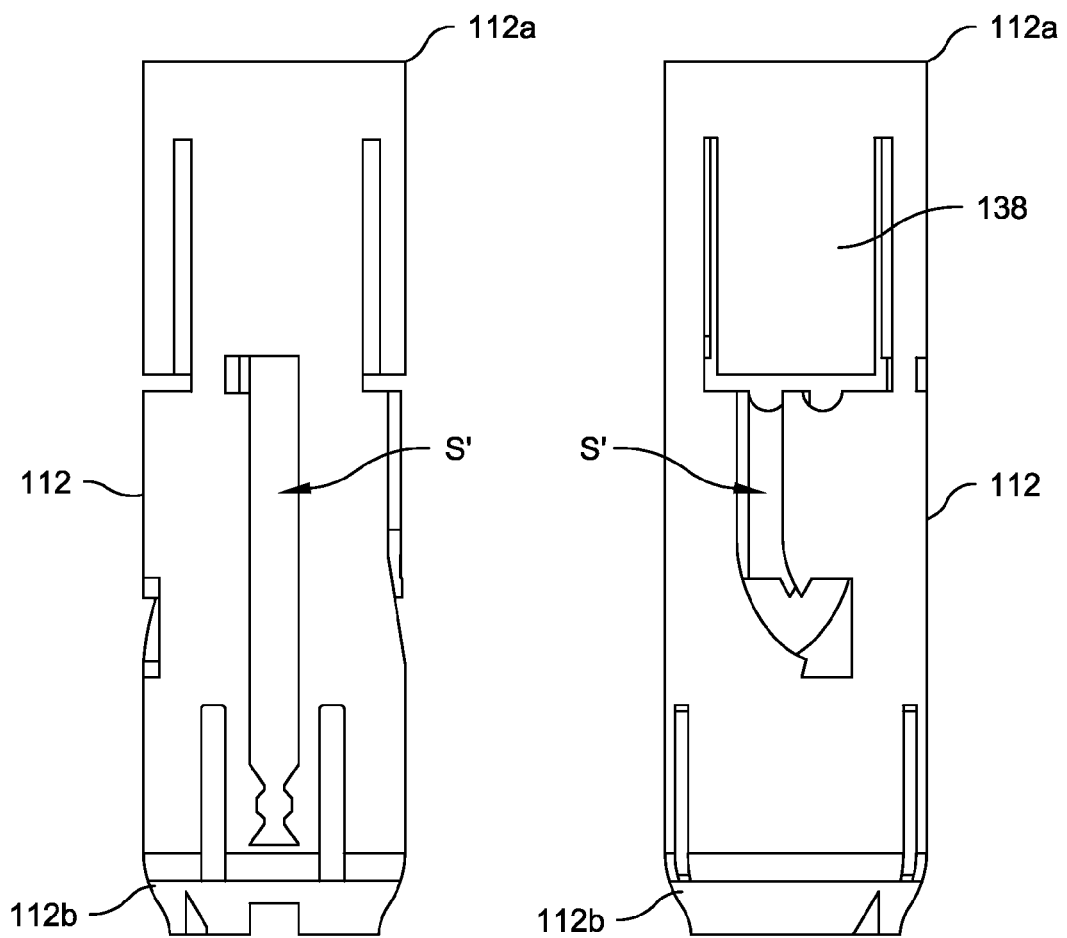
*Fig. 10*     *Fig. 11*

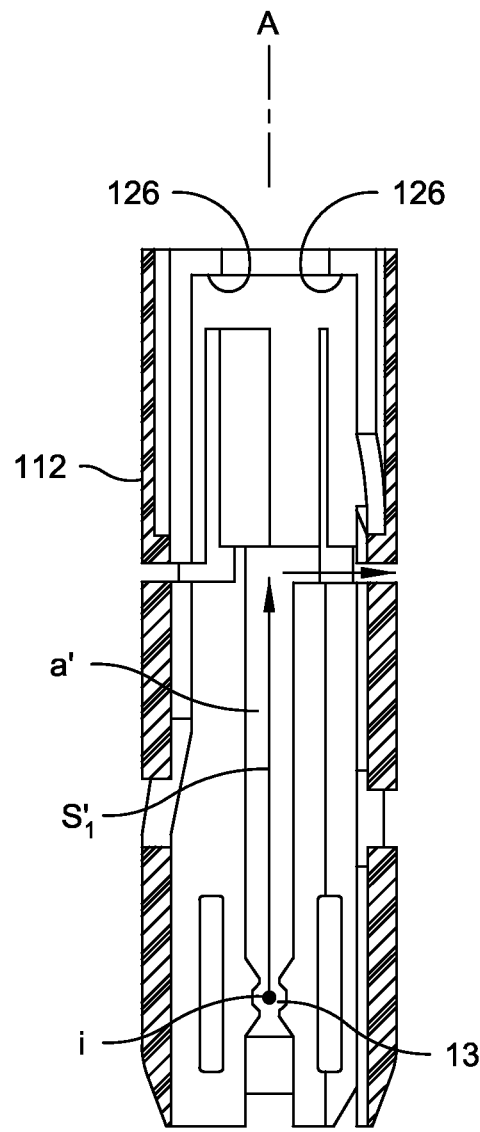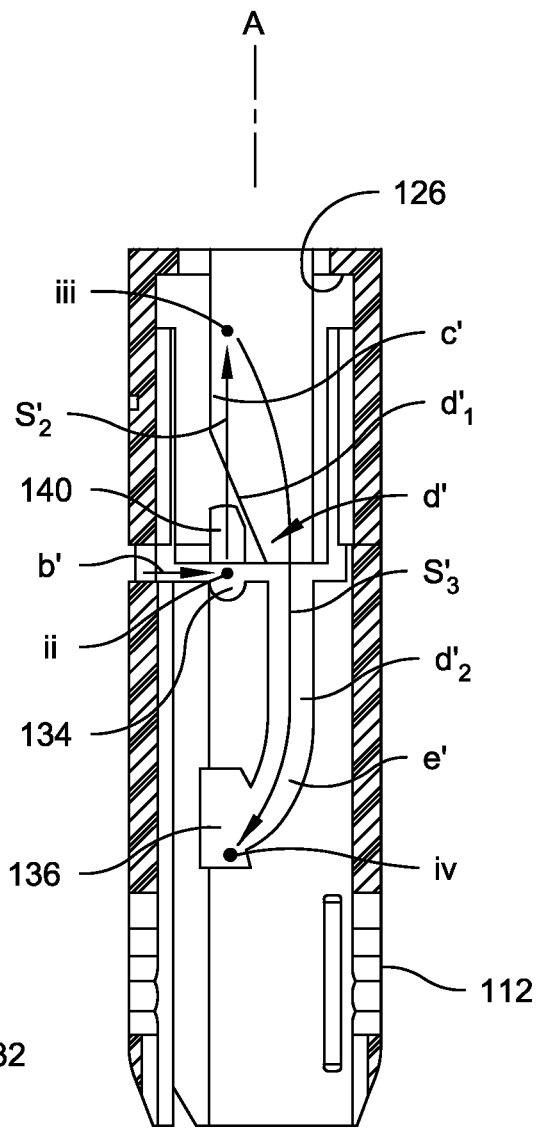
*Fig. 12*  *Fig. 13*

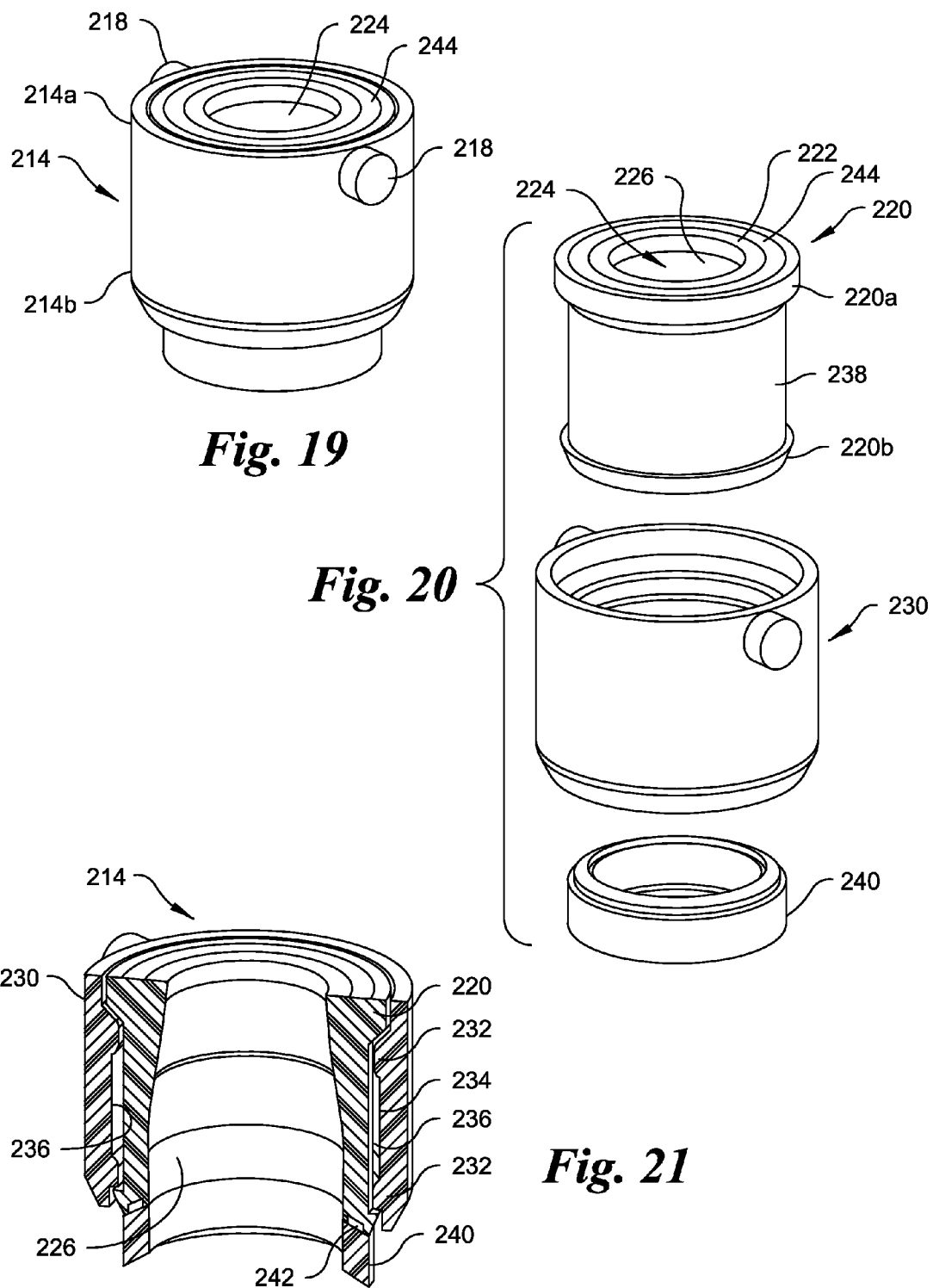

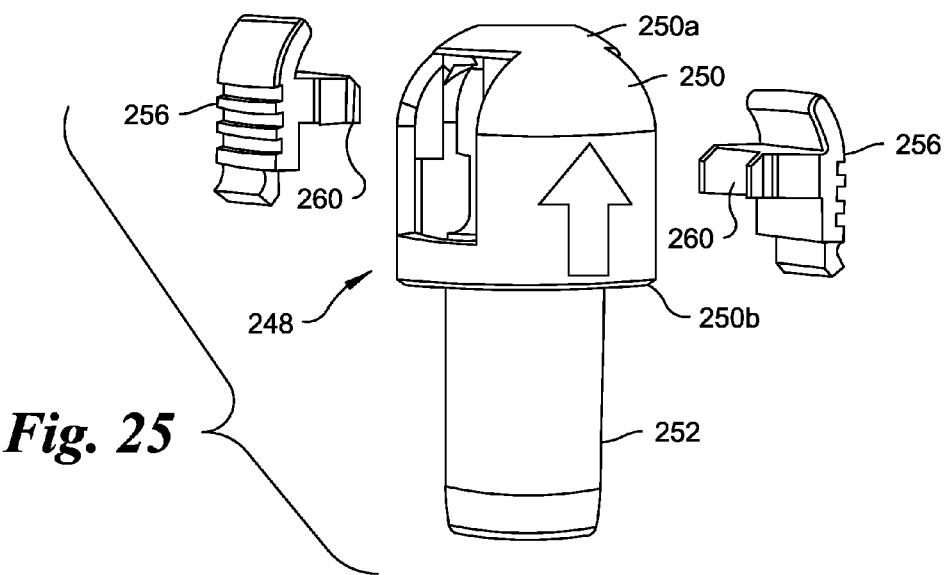
*Fig. 25*
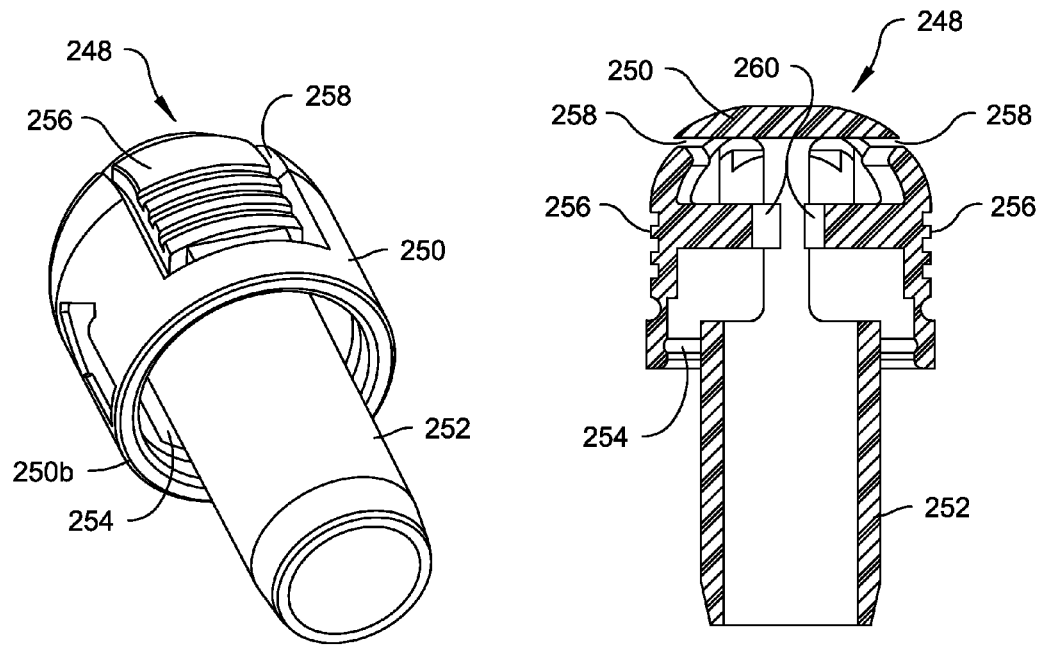
*Fig. 26*     *Fig. 27*

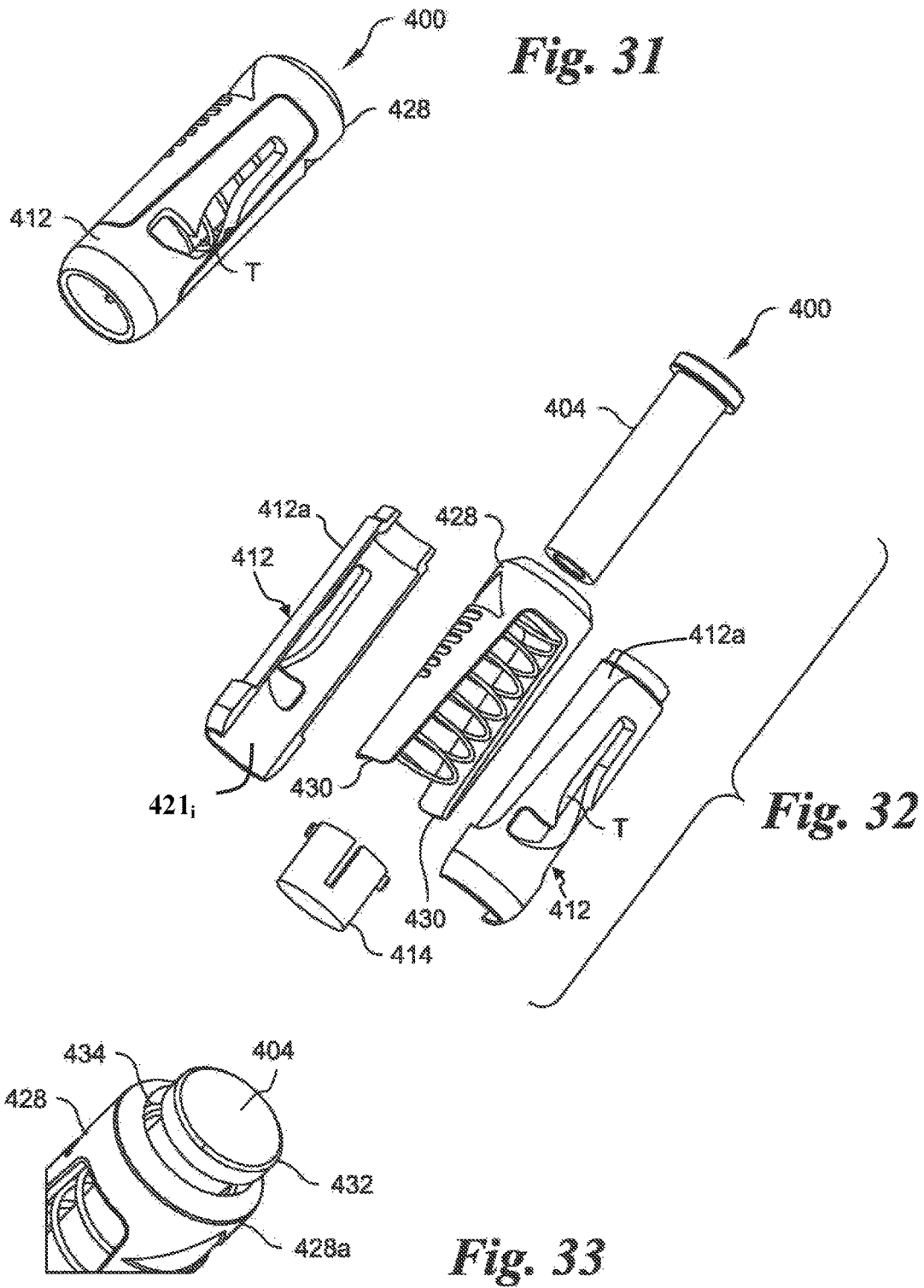

LOW RADIAL PROFILE NEEDLE SAFETY DEVICE

CROSS-REFERENCE TO RELATED APPLICATIONS

This application is a continuation in-part of U.S. patent application Ser. No. 14/383,364 filed Sep. 5, 2014, which is a Section 371 of International Application No. PCT/US2013/029518, filed Mar. 7, 2013, which was published in the English language on Sep. 12, 2013 under International Publication No. WO 2013/13446, which claims the benefit of U.S. Provisional Patent Application No. 61/607,711, filed Mar. 7, 2012.

BACKGROUND OF THE INVENTION

The present invention is directed to a low radial profile needle safety shield for syringes, in general, and for pharmaceutical syringes in particular.

Needlestick injuries are a well known occupational hazard for healthcare workers. Unintended needlesticks have the potential for transmitting blood-borne viruses such as hepatitis B and C and the human immunodeficiency virus (HIV) to the recipient. After a needlestick injury, certain procedures must be followed to minimize the risk of infection for the recipient, such as laboratory blood tests and post-exposure prophylaxis started immediately after exposure to a pathogen, such as one of the aforementioned viruses, in order to prevent infection by the pathogen and the development of the associated disease.

Conventional safety devices intended to reduce the frequency of post-injection needlesticks typically have a sheath partially or completely surrounding the pharmaceutical syringe. The sheath may be held in a retracted position exposing the needle for aspiration and injection and may be automatically deployed around a needle afterwards.

Among the drawbacks of many conventional prior art needle safety devices is that they are not compatible with current accepted practice due to sizes and configurations that are incompatible with conventional filling and sterilization equipment and methods.

Accordingly, there is a need in the art for a safety injection device having a low radial profile.

BRIEF SUMMARY OF THE INVENTION

Briefly stated, one aspect of the invention is a needle safety device for an injection device having a generally cylindrical barrel with a distal end from which a cannula extends. The needle safety device has an outer tube within which the barrel is slideably receivable. The outer tube has a distal end and a proximal end. A collar in the outer tube is moveable relative thereto and is rotatably attachable to the distal end of the barrel. A force member is between the outer tube and the collar and biases the outer tube in a distal direction. A track is formed in the inner surface of the outer tube. A pin extending radially outwardly from the collar slidingly engages the track. The track comprises a first track segment extending from a staging position to a pre-injection position. The proximal end of the outer tube is in registry with the distal end of the barrel allowing the barrel to be inspected when the collar is attached to the distal end of the barrel and the pin is in the staging position. The cannula extends a first length beyond the distal end of the outer tube when the collar is attached to the distal end of the barrel and the pin is in the pre-injection position. A second track segment contiguous with the first track segment extends from the pre-injection position to a full-insertion position. The cannula extends a second length greater than the first length from the distal end of the outer tube when the collar is attached to the distal end of the barrel and the pin is in the full-insertion position. A third track segment contiguous with the second track segment extends from the full-insertion position to a locked position in which the pin is immovably retainable. The cannula is entirely within the outer tube when the collar is attached to the distal end of the barrel and the pin is immovably retained in the locked position.

Another aspect of the invention is a needle safety device for an injection device having a generally cylindrical barrel with a distal end having a hub from which a cannula extends. The needle safety device has an outer tube within which the barrel is slideably receivable. The outer tube has a longitudinal axis along which the outer tube is movable in a distal direction to an extended position and in a proximal direction opposite the distal direction to a retracted position. A track is formed in an inner surface of the outer tube. A collar within the outer tube is attachable to the distal end of the barrel and has a radially outwardly extending collar pin slideably engaging the track. A cap is removably attached to a distal end of the outer tube. A cannula shield is within the outer tube. The cannula shield has a proximal end removably engaging the collar and a distal end within the cap and to which the cap is attached. A biasing member within the outer tube applies in the distal direction a biasing force to the outer tube. The cannula is in the cannula shield and entirely within the outer tube when the collar is attached to the distal end of the barrel and the collar pin is in a pre-injection position in the track. The cannula extends beyond the distal end of the outer tube when the collar is attached to the distal end of the barrel, the cannula shield and cap are removed from the outer tube and the collar pin is in a full-insertion position in the track. The cannula is irreversibly retained entirely within the outer tube when the collar is attached to the distal end of the barrel and the collar pin is in a locking position in the track.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 3 is an side cross-sectional view of the safety device of FIG. 1;

FIG. 4 is a side perspective view of the outer tube of the safety device of FIG. 1;

FIG. 8 is a side perspective view of another embodiment of the low radial-profile needle safety device in a staging position on the barrel of a pharmaceutical injection device in accordance with the present invention;

FIG. 9 is an exploded side perspective view of the needle safety device of FIG. 8, FIG. 10 is an side cross-sectional view of the safety device of FIG. 8;

FIG. 11 is a front elevation view of the outer tube of the safety device of FIG. 8;

FIG. 12 is a right side elevation view of the outer tube of the safety device of FIG. 8;

FIG. 13 is a side cross-sectional view of the outer tube of the safety device of FIG. 8;

FIG. 19 is a top perspective view of the collar of FIG. 18;

FIG. 20 is an exploded top perspective view of the collar of FIG. 19;

FIG. 21 is a top perspective cross section view of the collar of FIG. 19;

FIG. 25 is an enlarged exploded side perspective view of the cap of FIG. 18;

FIG. 26 is a bottom perspective view of the cap of FIG. 18;

FIG. 27 is side cross section view of the cap of FIG. 18;

FIG. 31 is a side perspective view of another embodiment of the low radial-profile needle safety device in accordance with the present invention;

FIG. 32 is an exploded side perspective view of the needle safety device of FIG. 31; and FIG. 33 is an enlarged top perspective view of a portion of the low radial-profile needle safety device of FIG. 31.

DETAILED DESCRIPTION OF THE INVENTION

Figures 1, 2:
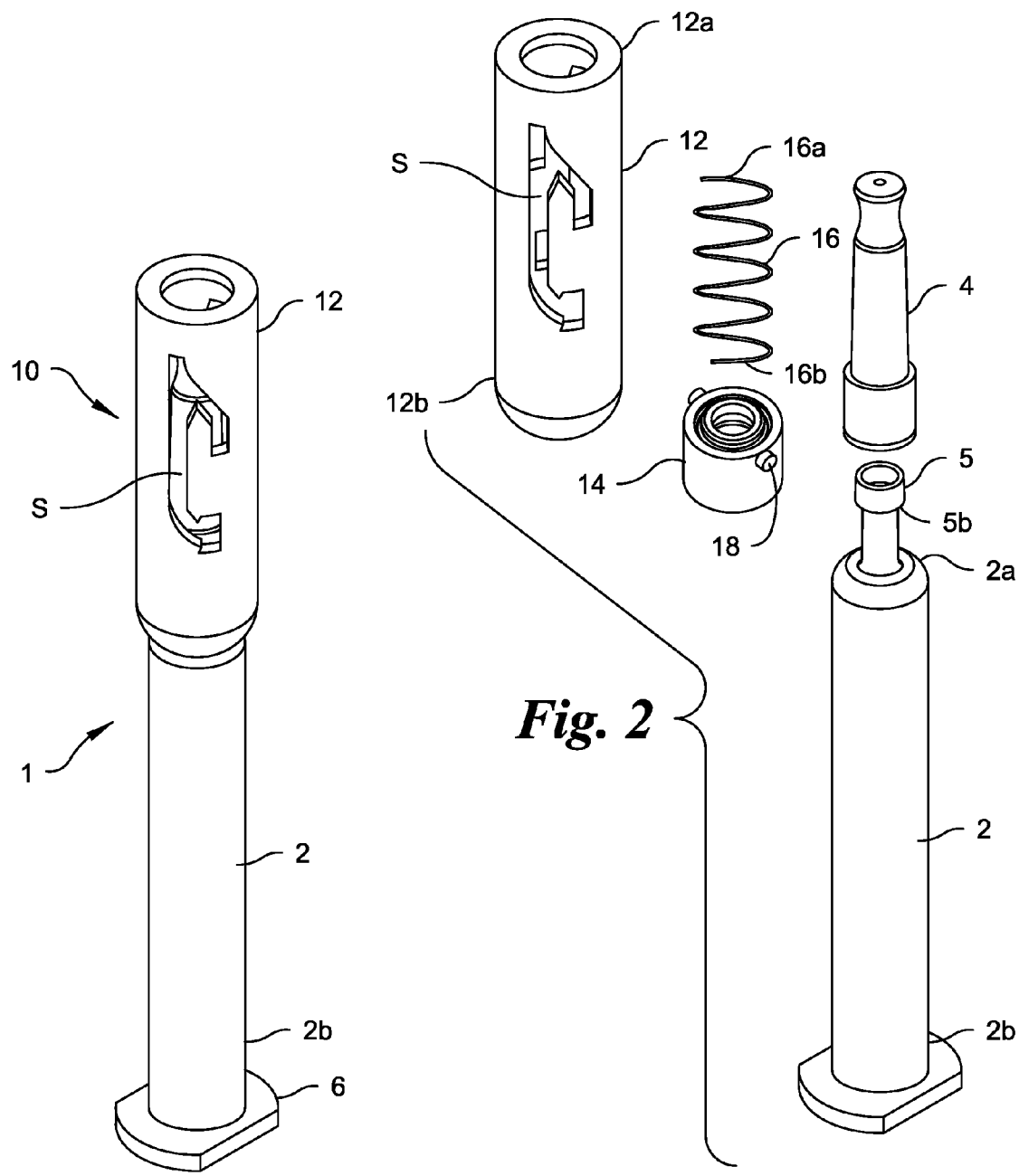
FIG. 1 is a side perspective view of an embodiment of the low radial-profile needle safety device in a staging position on the barrel of a pharmaceutical injection device in accordance with the present invention.
FIG. 2 is an exploded side perspective view of the needle safety device of FIG. 1.

Reference will now be made in detail to embodiments of the invention, examples of which are illustrated in the accompanying drawings. The terminology used in the description of the invention herein is for the purpose of describing particular embodiments only and is not intended to be limiting of the invention.

As used in the description of the invention and the appended claims, the singular forms "a", "an" and "the" are intended to include the plural forms as well, unless the context clearly indicates otherwise. The words "and/or" as used herein refers to and encompasses any and all possible combinations of one or more of the associated listed items. The words "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The words "right," "left," "lower" and "upper" designate directions in the drawings to which reference is made. The words "inwardly" and "outwardly" refer to directions toward and away from, respectively, the geometric center of the needle safety shield, and designated parts thereof. The terminology includes the words noted above, derivatives thereof and words of similar import.

Although the words first, second, etc., are used herein to describe various elements, these elements should not be limited by these words. These words are only used to distinguish one element from another. For example, a first segment could be termed a second segment, and, similarly, a second segment could be termed a first segment, without departing from the scope of the present invention.

As used herein, the word "distal" means in a direction away from the hand of a user holding the injection device immediately prior to injecting a medicament (e.g., the end of the barrel from which the cannula extends is the distal end of the barrel) and "proximal" means toward the hand of a user holding the injection device immediately prior to injecting a medicament.

The following descriptions are directed towards various embodiments of a needle safety shield in accordance with the present invention.

Referring to the drawings in detail, where like numerals indicate like elements throughout, there is shown in FIGS. 1-7 a preferred embodiment of a low radial profile needle safety device, generally designated 10, and hereinafter referred to as the "safety device" 10 in accordance with the present invention. The safety device 10 is for use with an injection device 1, such as a pharmaceutical syringe. The injection device 1 may be a pre-filled; however, the present invention is not so limited. For example, the injection device 1 may be nearly any type of pharmaceutical syringe, including those to be filled by a patient or user, for example.

The injection device 1 preferably has a generally cylindrical barrel 2 having a distal end 2a and an opposing proximal end 2b. A cannula (or needle) 3 extends from the distal end 2a of the barrel 2 and is in fluid communication with a bore of the barrel 2. The cannula 3 may be removably attached to the distal end 2a of the barrel 2. Alternatively, and preferably, the cannula 3 is fixedly attached thereto. A removable shield 4 covers the cannula 3. Typically, the distal end 2a of the barrel 2 is configured as a tapered hub 5 that may have a variety of configurations, such as an inverted frustum, a cylinder or a sphere, and the proximal end 2b of the barrel 2 has a radially outwardly extending finger flange 6. Preferably, the hub 5 has a generally circular or bulbous shape that extends radially outwardly or beyond at least some other portion of the distal end 2a of the barrel 2. However, the hub 5 is not limited to the size, shape and/or configuration shown and described herein Although the barrel 2 may be formed of nearly any material capable of safely enclosing medicaments, it is preferably formed of glass or a polymeric material. The injection device 1 may be pre-filled with a medicament or may be provided without a medicament for filling by the user.

A piston 7 slidably receivable in the bore of the barrel 2 is attached to a piston rod 8 having a free proximal end 8b that extends from the proximal end 2b of the barrel 2.

The safety device 10 comprises an outer tube 12 within which the barrel 2 is slideably receivable. The outer tube 12 has a distal end 12a, a proximal end 12b and a longitudinal axis A. A collar 14 is in the outer tube 12 and is movable relative thereto. In some embodiments, the collar 14 is fixedly attachable to the distal end 2a of the barrel 2. In other embodiments, the collar 14 is rotatably attachable to the distal end 2a of the barrel 2. A three member 16, such as a compressible coil spring, is provided between the outer tube 12 and the collar 14. The force member biases the outer tube 12 in a distal direction. A track S is formed in the inner surface of the outer tube 12. A pin 18 extending radially outwardly from the collar 14 slidingly engages the track S which, in turn, guides the movement of the pin 18 and therefore the collar 14 within the outer tube 12.

Figure 7:
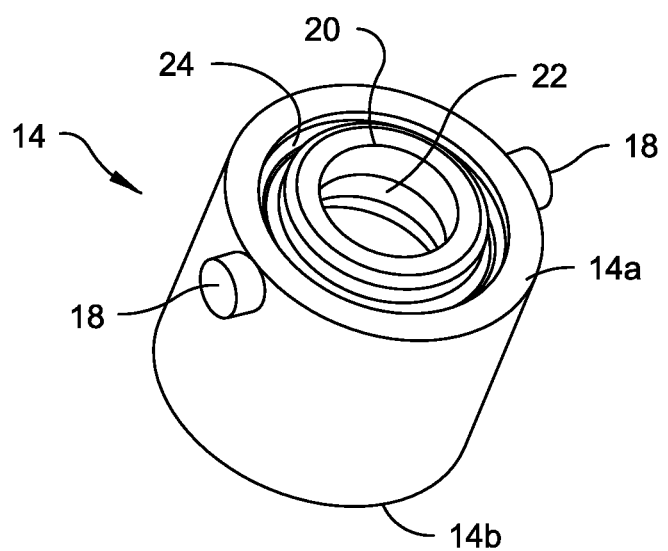
FIG. 7 is a top perspective view of the collar of the safety of FIG. 1.

Referring to FIG. 7, in a preferred embodiment, the collar 14 has the general shape of a hollow cylinder terminating at the distal end with an annulus 20 having a central bore 22 sized to receive and retain the distal end 2a of the barrel 2 or the hub 5 if the distal end 2a of the barrel 2 is configured as a hub. The annulus 20 is sufficiently compliant and sized to allow passage of the hub 5 through the bore 22 and thereafter to rotatably engage the hub 5. The outer surface of the annulus 20 has a generally circular channel 24 to receive the proximal end 16b end of the force member (e.g., a coil spring) 16. A circumferential step 26 (see, FIG. 3) in the inner surface of the outer tube 12 is sized to receive and engage the distal end 16a of the force member 16. At least one pin 18 extends radially outwardly form the collar 18 and is slidably receivable in the track S. In embodiments in which the outer tube 12 has a plurality of tracks, the collar 14 may have a corresponding plurality of pins.

To mount the collar 14 to the barrel 2, the distal end 2a of the barrel 2 or the hub 5 may be inserted into and through the proximal end 14b of the collar 14 and into and through the distal end 14a of the collar 14. As the hub 5 passes through the distal end 14a of the collar 14, the bore 22 in the annulus 20 expands until the hub 5 passes completely therethrough. The annulus 20 then return to its initial state in which the distal end 14a of the collar 14 abuts the proximal surface 5b of the hub 5, thereby rotatably attaching the collar 14 on the barrel 2 between the hub 5 and a shoulder or enlarged portion of the distal end 2a of the barrel 2.

Figures 5, 6:
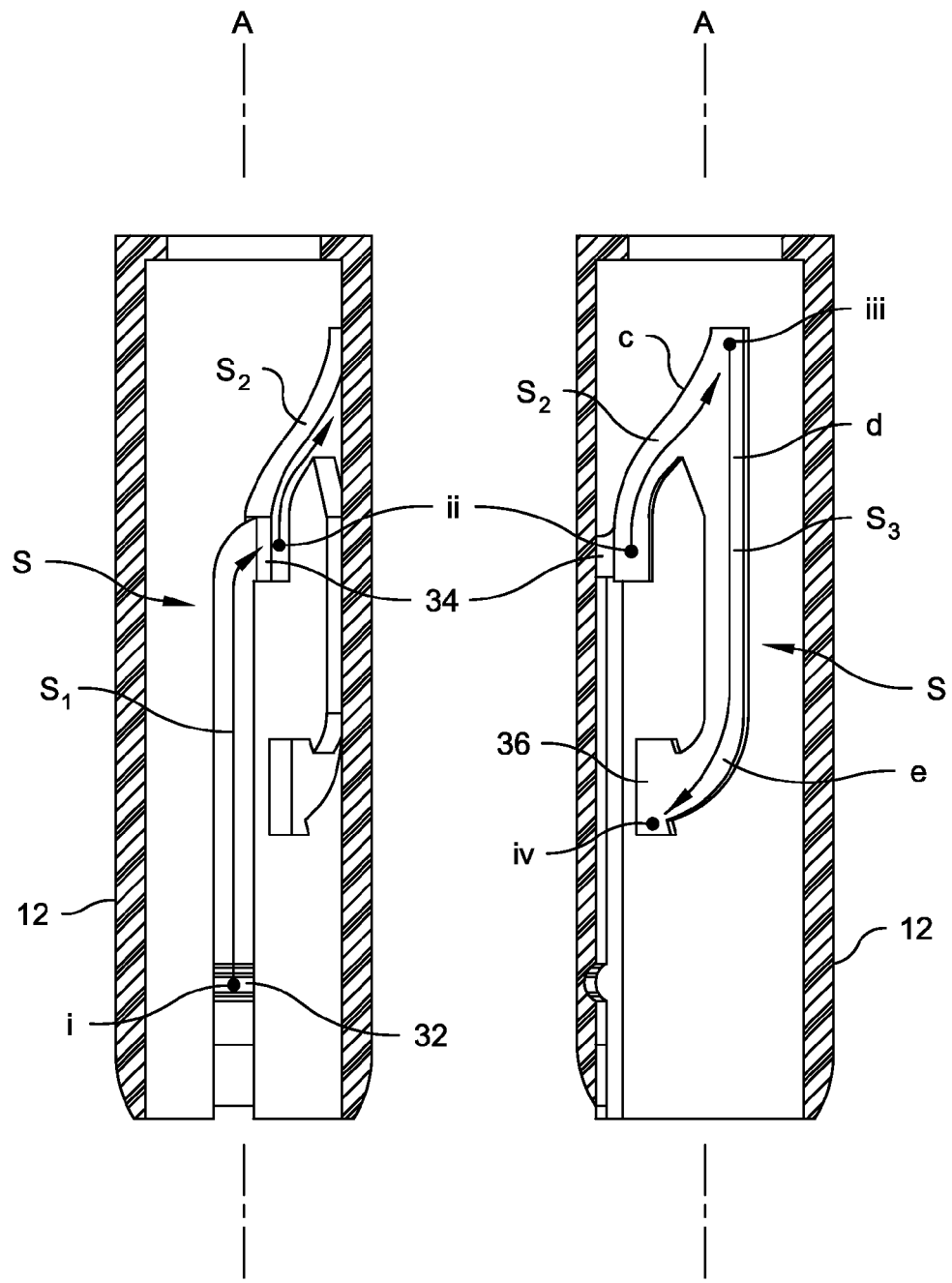
FIGS. 5 and 6 are side cross-sectional views of the outer tube of the safety device of FIG. 1 showing the track in the outer tube.

Referring to FIGS. 5 and 6, in some embodiments, the track S comprises three track segments. A first track segment $S_1$ is provided to allow the safety device 10 to be assembled and inspected after the collar 14 has been attachment to the distal end 2a of the barrel 2 as discussed above. The first track segment $S_1$ extends from a staging position (i) shown in FIG. 15A having a first catch 32 to a pre-injection position (ii) shown in FIG. 15B having a second catch 34 and has as a profile an initial portion (a) substantially parallel to the longitudinal axis A of the outer tube 12 followed by a final portion (b) angled with respect to the longitudinal axis A and serving as a cammed surface. When the collar 14 is attached to the distal end 2a of the barrel 2 and the pin 18 is in the staging position (i), the proximal end 12b of the outer tube 12 is in registry with the distal end 2a of the barrel 2 allowing the barrel 2 to be inspected.

During the assembly process, the force element 16 is inserted in the outer tube 12. The collar 14, attached to the distal end 2a of the barrel 2, is then inserted in the outer tube 12 such that the pin 18 (or plurality of pins, if there is a plurality of tracks) is in the first track segment $S_1$ (or plurality of first track segments). The outer tube 12 is moved in the proximal direction causing an initial compression of the force element 16 as the pin 18 travels to the beginning of the first track segment $S_1$ and becomes releasably retained in the first catch 32 thereby securing the outer tube 12 in the staging position (i).

As the outer tube 12 moves in the proximal direction causing the force member 16 to be compressed, the pin 18 travels the initial portion of the first track segment $S_1$ and is guided to the pre-injection position (ii) by the cammed surface which imparts an angular rotation to the collar releasably securing the pin 18 in second catch 34 When the collar 14 is attached to the distal end 2a of the barrel 2 and the pin 18 is in the second catch 34, the cannula 3 extends a first length $L_1$ beyond the distal end of the outer tube 12. The length $L_1$ of cannula extension depends on the particular size and configuration of the insertion device 1. At a minimum the length of extension allows visualization of the distal most tip of the cannula 3 at an insertion location prior to penetration of the skin.

Figure 15:
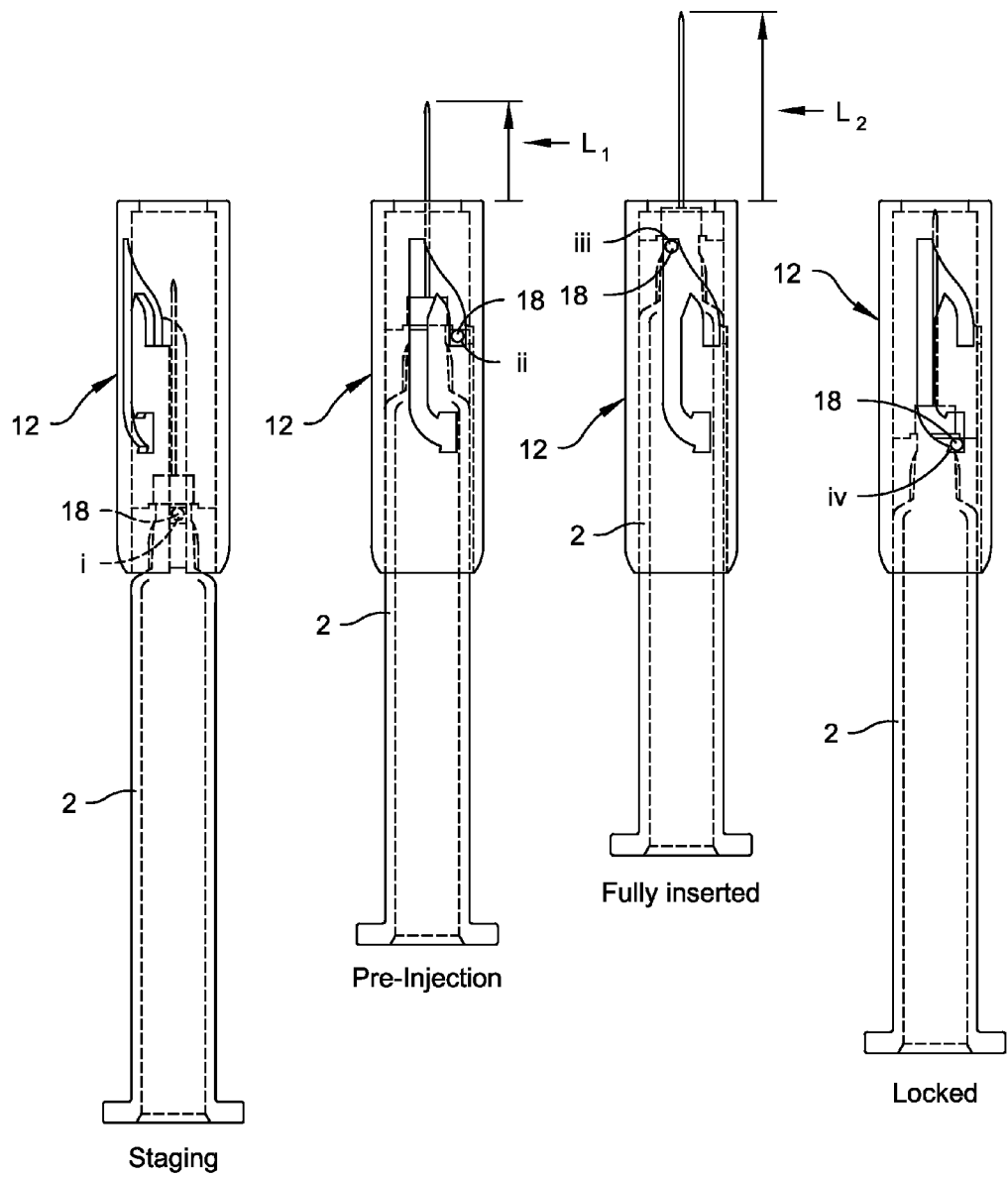
FIGS. 15A-15D are a sequence of side elevation views of the safety device and a portion of a pharmaceutical syringe of FIG. 1 showing progressive positions of the safety device relative to the pharmaceutical insertion device.
Figure 16:
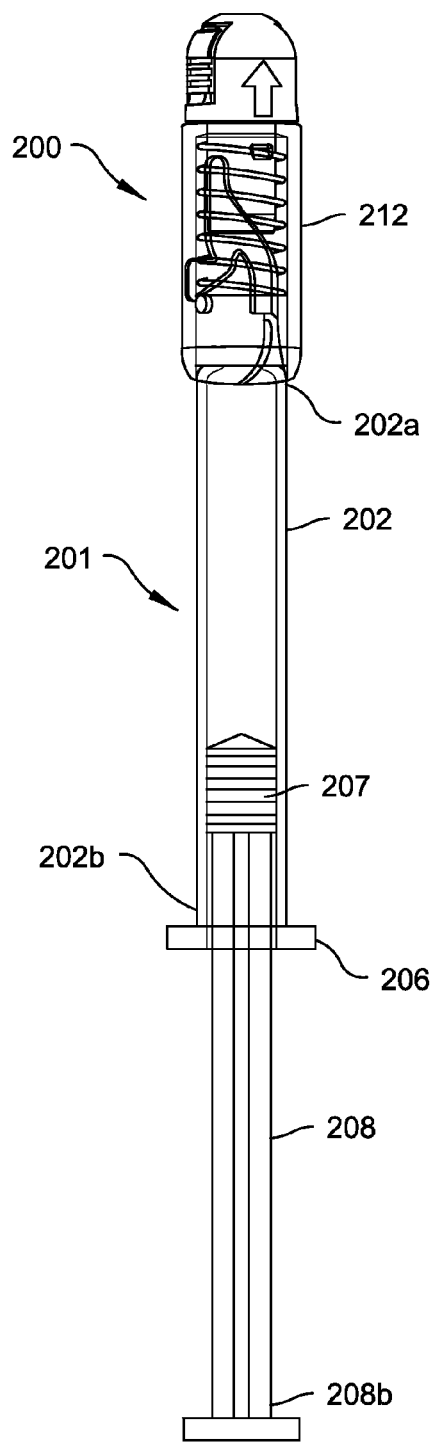
FIG. 16 is a partially transparent side elevation view of an embodiment of the low radial-profile needle safety device attached to an injection device in accordance with the present invention.
Figure 17:
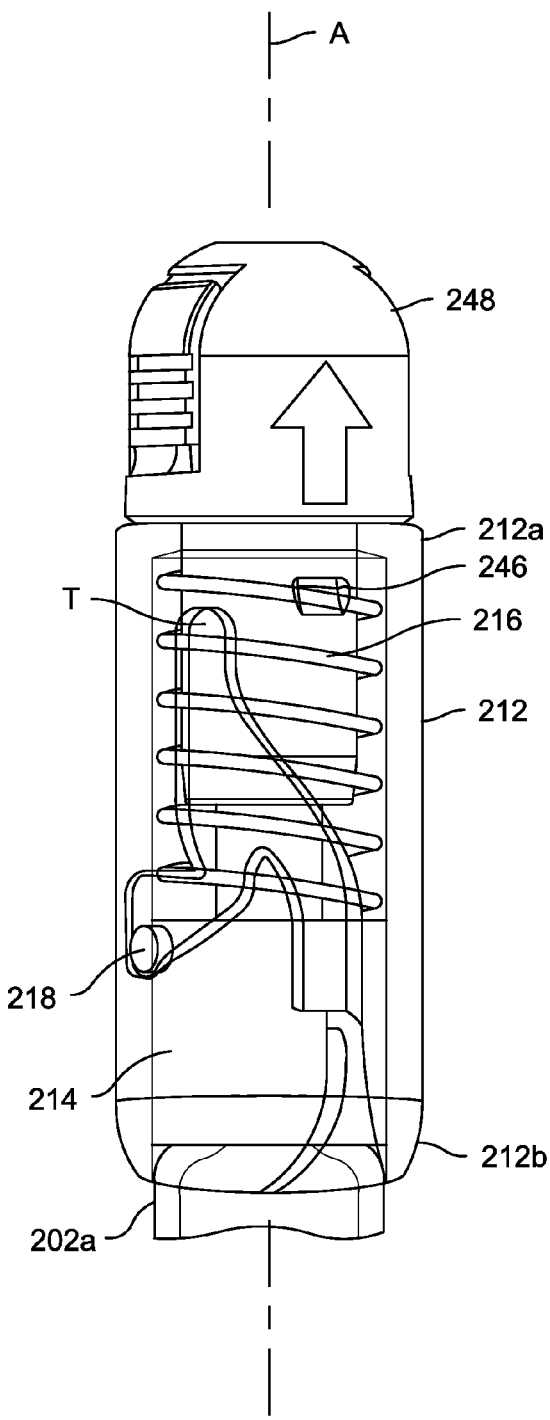
FIG. 17 is an enlarged partially transparent side elevation view of the safety device of FIG. 16.
Figure 18:
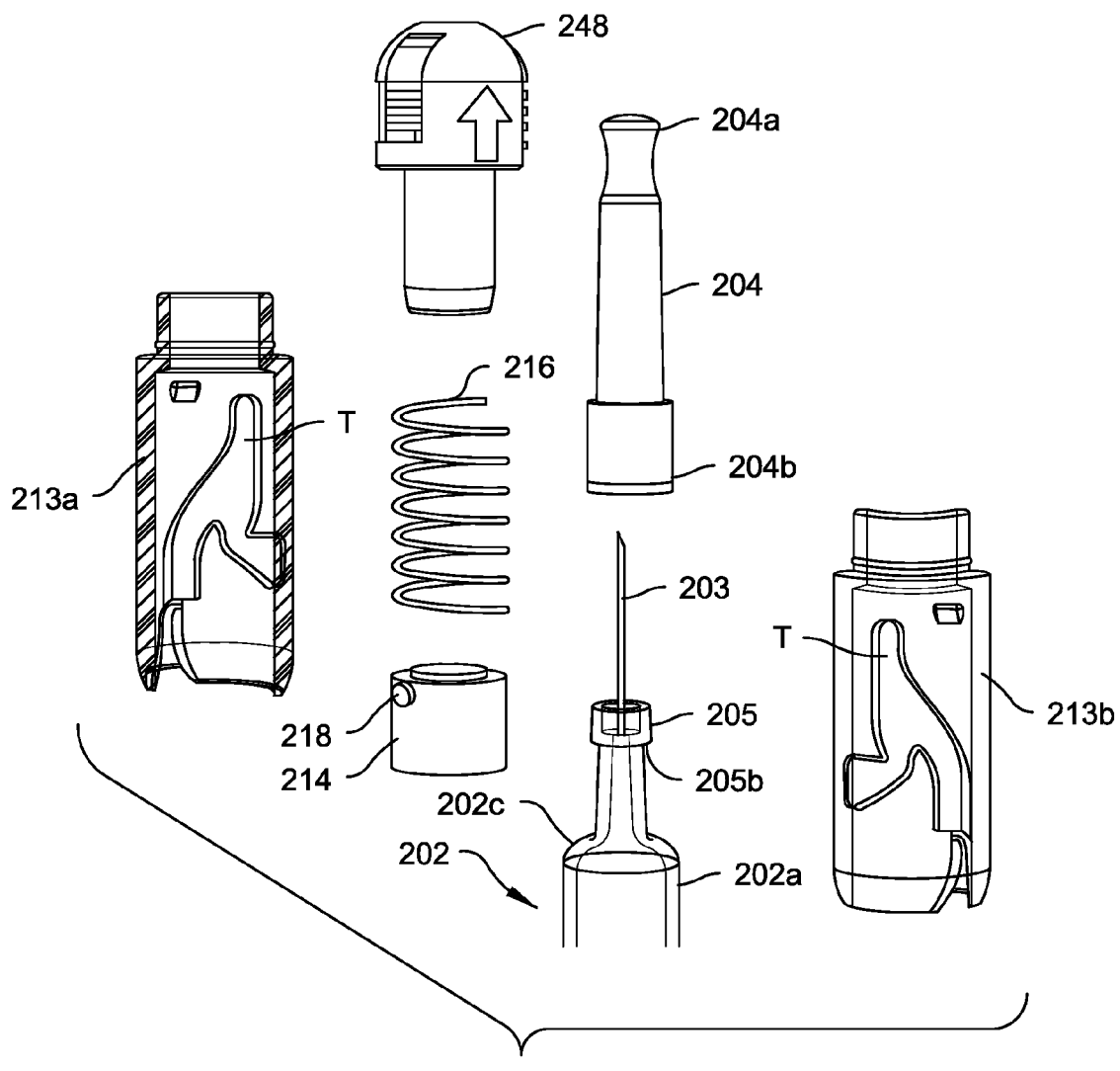
FIG. 18 is an exploded view of the safety device of FIG. 17.
Figure 22:
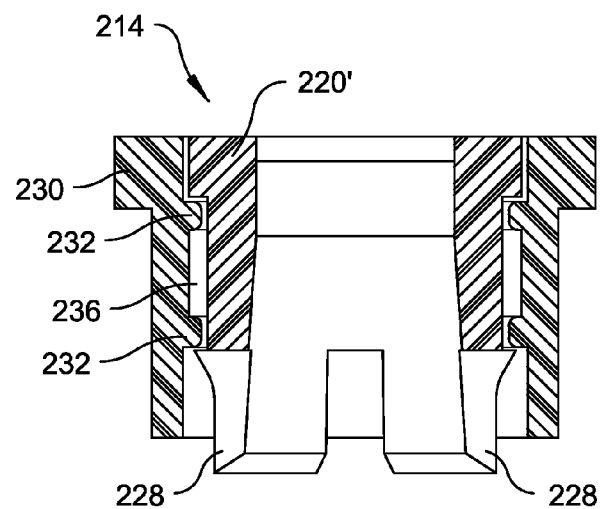
FIG. 22 is a side cross section view of another embodiment of a collar for the safety device of FIG. 17.
Figure 23:
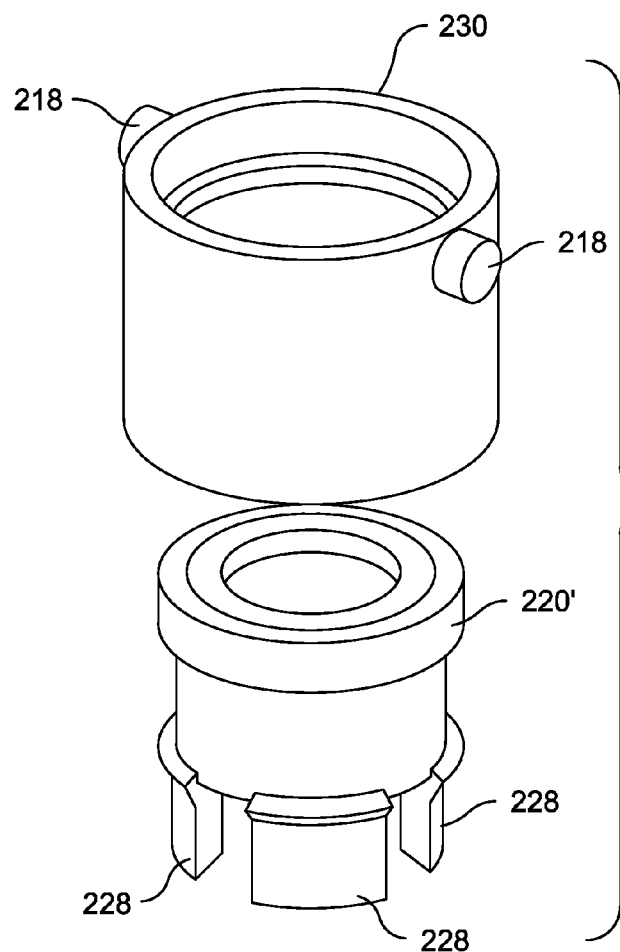
FIG. 23 is an exploded top perspective view of the collar of FIG. 22.

A second track segment $S_2$ contiguous with the first track segment $S_1$ extends from the pre-injection position (ii) to a full-insertion position (iii) shown in FIG. 15C. The second track segment $S_2$ is angled with respect to the longitudinal axis of the outer tube 12 and has an arcuate profile (c).

At the initiation of an injection, the distal end 12a of the outer tube 12 makes contact with the skin. The force applied by the skin to the outer tube 12 moves the pin 18 out of the first catch 32 and along beginning of the second track segment $S_2$. As the skin is being penetrated by the cannula 3, continued application of force by the skin to the outer tube 12 further moves the outer tube 12 in the proximal direction and the pin 18 in the distal direction along the second track segment $S_2$ to the fully inserted position (iii). When the collar 14 is attached to the distal end 2a of the barrel 2 and the pin 18 is in the full-insertion position (iii), the cannula 3 extends a second length $L_2$ greater than the first length $L_1$ from the distal end 12a of the outer tube 12. The length $L_2$ of cannula extension at the full-insertion position (iii) depends on the particular size and configuration of the insertion device 1 and the subcutaneous location the medicament is to be delivered. The second track segment guides the pin 18 along a generally arcuate path imparting both axial translation and rotation to the collar 14. The outer tube 12 remains in the full-insertion position (iii) until withdrawal of the cannula 3 is initiated, typically after a full dose of the medicament is delivered.

A third track segment $S_3$ contiguous with the second track segment $S_2$ extends from the full-insertion position (iii) to a locked position (iv) shown in FIG. 15D having a third catch 36 in which the pin 18 is immovably retainable. The third track segment $S_3$ has an initial portion (d) extending from the full-insertion position (iii) substantially parallel to the longitudinal axis of the outer tube followed by an arcuate profile (e) providing a cammed surface terminating in an axially extending locked position (iv). As the cannula 3 is being withdrawn after the desired dose of medicament has been delivered, the force applied by the skin to the outer tube 12 decreases and the outer tube 12 moves in the distal direction relative to the collar 14 under the reactive force of the force member 16 compressed between the collar and the outer tube. The third track segment $S_3$ initially guides the pin 18 substantially parallel to the longitudinal axis and then along a generally arcuate path imparting both axial translation and a rotation to the collar and finally into the locked position (iv). When the collar 14 is attached to the distal end 2a of the barrel 2 and the pin 18 is immovably retained in the third catch 36, the outer tube 12 fully covers the cannula 3 in the entirety and is prevented from moving in either the proximal or distal directions.

Referring to the drawings in detail, where like numerals indicate like elements throughout, there is shown in FIGS. 8-14 another preferred embodiment of a low radial profile needle safety device, generally designated 100, and hereinafter referred to as the "safety device" 100 in accordance with the present invention. The safety device 100 is also for use with the injection device 1 disclosed above.

The safety device 100 comprises an outer tube 112 configured to slidably receive therein a portion of the distal end 2a of the barrel 2. At least one track S' is formed in the inner surface of the outer tube 112. The at least one track S' has a plurality of contiguous segments further discussed below. In some embodiments, the inner surface may have a plurality of tracks, each having the same configuration, positioned in a spaced-apart, aligned arrangement. A portion of the outer tube 112 has a generally U-shaped cut therethrough forming a flexible tongue 138 having a radially disposed ramp 140.

A collar 114 is slidably received in the outer tube 112. The collar 114 is attachable to the distal end 2a of the barrel 2. At least one pin 118 extends radially outwardly from a sidewall of the collar 114 and is slidably received in the at least one track S' formed in the inner surface of the outer tube 112. In embodiments in which the outer tube 112 may have a plurality of tracks S', the collar 114 may have a corresponding plurality of pins 118 projecting radially outwardly from spaced-apart locations around the circumference of the sidewall. A force member 116 extending between the outer tube 112 and the collar 114 biases the outer tube 112 in a distal direction. In some embodiments, opposed ends of the force member 116 may be received and retained in a circumferential channel 124 in the outer surface of the collar 114 and a circumferential step 126 in the inner surface of the distal end 112a of the outer tube 112.

Figure 14:
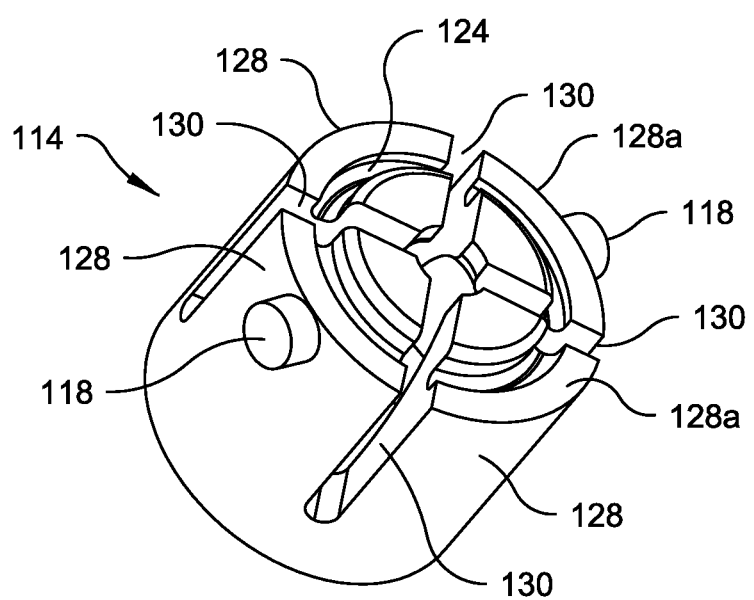
FIG. 14 is a top plan view of the collar of FIG. 8.

Referring to FIG. 14, in a preferred embodiment, the collar 114 is a body of revolution having a bore 122 therethrough and includes at least one finger 128, desirably a plurality of fingers 128 and preferably four spaced-apart fingers 128 fixedly attachable to the distal end 2a of the barrel 2. Each finger 128 is sufficiently compliant to allow passage of the hub 5 through the bore 122 of the collar 114 and then to return to an initial configuration. Each finger 128 preferable is configured to conform to the size and/or shape of a corresponding portion of the distal end 2a of the barrel 2. A gap or spacing 130 is preferably located between adjacent fingers 128, which allows for the collective expansion and contraction of the four fingers 128.

A channel formed in the distal end 128a of each finger 128 collectively forms the circular channel 124 in the outer surface of the collar 114 to receive one end of the force element 116. A circumferential step 126 (see, FIGS. 12 and 13) in the inner surface of the outer tube 112 is sized to receive and engage the distal end of the force member 116. Diametrically opposed pins 118 extends radially outwardly from the collar 114 and are sized to slidingly engage the at least one track S' formed in the inner surface of the outer tube 112.

To mount the collar 114 to the barrel 2, the hub 5 may be inserted into and through the proximal end 114b of the collar 114 and into and through the distal end 114a of the collar 114. As the hub 5 passes through the distal end 114a of the collar 114, each of the fingers 128 may flex radially outwardly from the longitudinal axis A until the hub 5 passes completely therethrough. The fingers 128 then return to their initial state in which the distal end 128a of each finger 128 abuts the proximal surface 5b of the hub 5, thereby immovably attaching the collar 114 in place on the barrel 2 between the hub 5 and a shoulder or enlarged portion of the distal end 2a of the barrel 2. In some embodiments, the hub 5 may have a portion below the proximal surface 5b having ribs that extend into the gaps 130 between the fingers 128 further preventing rotation of the collar 114.

Referring to FIGS. 12 and 13, in a preferred embodiment, the track S' has a plurality of segments, each segment corresponding to a relative position of the outer tube 112 with respect to the distal end 2a of the barrel 2 and/or to the cannula 3 projecting from the hub 5.

A first track segment $S_1'$ is provided to allow the safety device 100 to be assembled and inspected after the collar 114 has been attachment to the distal end 2a of the barrel 2 as discussed above. The first track segment $S_1'$ extends from a staging position (i) having a first catch 132 to a pre-injection position (ii) having a second catch 134 and has as a profile an initial portion a' substantially parallel to the longitudinal axis of the outer tube followed by a circumferential portion b' terminating in the catch 134 in registry with the radially disposed ramp 140 on the flexible tongue 138 of the outer tube 112. When the collar 114 is attached to the distal end 2a of the barrel 2 and the pin 118 is in the staging position (i), the proximal end 112b of the outer tube 112 is in registry with the distal end 2a of the barrel 2 allowing the barrel 2 to be inspected.

During the assembly process, the force member 116 is inserted in the outer tube 112. The collar 118, attached to the distal end 2a of the barrel 2, is then inserted in the outer tube 112 such that the pins 118 are in the catch 132 at the staging position (i). The outer tube 112 is moved in the proximal direction causing the force member 116 to be compressed as the pins 118 travel the length of the initial portion a' of the first track segment $S_1'$. The outer tube 112 is then rotated to move the pins 118 along the circumferential portion b' until the pins 118 become releasably retained in the catch 134 thereby securing the outer tube 112 in the pre-injection position (ii). When the collar 114 is attached to the distal end 2a of the barrel 2 and the pin 118 is in the second catch 134, the cannula 3 extends a first length $L_1$ beyond the distal end of the outer tube 112.

A second track segment $S_2'$, contiguous with the first track section $S_1'$, extends substantially parallel to the longitudinal axis A of the outer tube 112 from the pre-injection position (ii) to the full-insertion position (iii) of the outer tube. At the initiation of an injection, the distal end 112a of the outer tube 112 makes contact with the skin. The force applied by the skin to the outer tube 112 causes the flexible tongue 138 to deflect radially outwardly as the pin 118 moves out of the first catch 132, up the radially disposed ramp 140 and along the second track segment $S_2'$. As the skin is being penetrated by the cannula 3, continued application of force by the skin to the outer tube 112 further moves the outer tube 112 in the proximal direction and the pins 118 in the distal direction along the second track segment $S_2'$ to the full-insertion position (iii). When the collar 114 is attached to the distal end 2a of the barrel 2 and the pin 118 is in the full-insertion position (iii), the cannula 3 extends a second length $L_2$ greater than the first length $L_1$ from the distal end 112a of the outer tube 112. The second track segment guides the pin 18 along a path substantially parallel to the longitudinal axis of the outer tube 112. The outer tube 112 remains in the full-insertion position (iii) until withdrawal of the cannula 3 is initiated, typically after a full dose of the medicament is delivered.

A third track segment $S_3'$, contiguous with the second track segment $S_2'$, has a profile having an initial portion c' extending from the fully inserted position (iii) substantially parallel to the longitudinal axis A of the outer tube 112 to a mid portion d' having a first extent $d_1'$ angled with respect to the longitudinal axis A followed by a second extent $d_2'$ parallel to the longitudinal axis A. The mid portion d' is followed by a final portion e' having an arcuate profile providing a cammed surface terminating in an axially extending locked position (iv).

After a full dose of the medicament has been delivered, and withdrawal of the cannula 3 is initiated, the force applied by the skin to the outer tube 112 decreases. Under the reactive force of the compressed force member 116, the outer tube 112 moves in the distal direction. The pins 118 move in the proximal direction along the third track segment $S_3'$ which guides the pins 118 in the initial portion c' substantially parallel to the longitudinal axis A imparting to the outer tube 112 translation in the axial direction without rotation. The first extent $d_1'$ of the mid portion d' cams the pins 118 in a direction angled with respect to the longitudinal axis A imparting to the outer tube 112 translation in the axial direction with rotation. The second extent $d_2'$ of the mid portion d' guides the pins 118 substantially parallel to the longitudinal axis A imparting to the outer tube 112 translation in the axial direction without rotation. The final portion e' of the third track segment $S_3'$ guides the pins 118 in a generally arcuate path imparting to the outer tube 112 both axial translation and a rotation until the pins 118 are in the locked position (iv) in the catch 136. In the locked position, the outer tube 112 is fully extended covering the cannula 3 in the entirety and is prevented from moving in the distal or proximal directions.

Referring to FIGS. 16-27 in detail, where like numerals indicate like elements throughout, there is shown another preferred embodiment of a low radial profile needle safety device, generally designated 200, and hereinafter referred to as the "safety device" 200 in accordance with the present invention. The safety device 200 is for use with an injection device 201, shown in FIGS. 16 and 18. The injection device 201 is substantially the same as the injection device 1 described above with the exception that a cannula shield 204 may be provided as part of the safety device 200.

The injection device 201 preferably has a generally cylindrical barrel 202 having a distal end 202a and an opposing proximal end 202b. A cannula (or needle) 203 extends from the distal end 202a of the barrel 202 and is in fluid communication with a bore of the barrel 202. The cannula 203 may be removably attached to the distal end 202a of the barrel 202. Alternatively, and preferably, the cannula 203 is fixedly attached thereto. Typically, the distal end 202a of the barrel 202 is configured as a tapered hub 205 that may have a variety of configurations, such as an inverted frustum, a cylinder or a sphere, and the proximal end 202b of the barrel 202 has a radially outwardly extending finger flange 206. Preferably, the hub 205 has a generally circular or bulbous shape that extends radially outwardly or beyond at least some other portion of the distal end 202a of the barrel 202. However, the hub 205 is not limited to the size, shape and/or configuration shown and described herein.

Although the barrel 202 may be formed of nearly any material capable of safely enclosing medicaments, it is preferably formed of glass or a polymeric material. The injection device 201 may be pre-filled with a medicament or may be provided without a medicament for filling by the user.

A piston 207 slidably receivable in the bore of the barrel 202 is attached to a piston rod 208 having a free proximal end 208b that extends from the proximal end 202b of the barrel 202.

The safety device 200 comprises an outer tube 212 within which the barrel 202 of the injection device 201 is slidably receivable. The outer tube 212 is preferably fabricated from a polymeric material as two molded first and second semi-cylindrical piece parts 213a, 213b, each a mirror image of the other, subsequently fused together to form the single unitary outer tube 212. The outer tube 212 has a distal end 212a, a proximal end 212b and a longitudinal axis "A" along which the outer tube 212 is movable in a distal, extended direction and in a proximal, retracted direction opposite the distal as further discussed below. A collar 214 slidably received in the outer tube 212 is rotatably attachable to the hub 205 at the distal end 202a of the barrel 202. A pair of diametrically opposed tracks "T" is formed in the inner surface of the outer tube 212 and receives therein collar pins 218 extending radially outwardly from the collar 214 to guide the collar 214 to a plurality of positions within the outer tube 212. A biasing member 216, such as a coil spring, extending between the outer tube 212 and the collar 214 biases the outer tube 212 in a distal direction away from the user. A cap 248 is removably attached to the distal end 212a of the outer tube 212.

Referring to FIGS. 19-21, in a preferred embodiment, the collar 214 is an assembly comprising at least a generally cylindrical inner body 220 fixedly attachable to the distal end 202a of the barrel 202 and a generally cylindrical outer body 230 which surrounds the inner body 220 and is rotatable relative thereto. The cylindrical inner body 220 has a distal end 220a with a compliant annular ring 222 having an annular ring bore 224 able to pass therethrough the distal end 202a of the barrel 202.

In some embodiments, the cylindrical inner body 220 may have a compliant inner sidewall 226 which may be fixedly attachable to the distal end 202a of the barrel 202 by radially inwardly directed restoration forces applied to the distal end 202a of the barrel 202 by the compliant sidewall 226 surrounding the distal end 202a of the barrel 202. In other embodiments, the collar assembly 214 may have a cylindrical inner body 220' fixedly attachable to the distal end 202a of the barrel 202 by a plurality of spaced-apart, radially inwardly biased flexible members 228. (See, FIGS. 22-23)

The cylindrical outer body 230 which surrounds the inner body 220 may be rotatably attached to the inner body 220 by at least one circumferential ring 232, and preferably by at least two spaced apart circumferential rings 232, extending radially inwardly from the inner surface 234 of the outer body 230 and received in an radially inwardly extending circumferential slot 236 in the outer surface 238 of the inner body 220. The circumferential ring 232 and slot 236 are sized such that the inner body 220 can be inserted in the outer body 230 by a snap fit while allowing rotation of the outer body 230 relative to the inner body 220.

In some embodiments, the assembly comprising the collar 214 may have a locking ring 240 which is attachable to the proximal end 220b of the inner body 220 in a tongue and groove interface 242. In other embodiments, the inner body 220 and the locking ring 240 may be a single unitary structure (not shown) fabricated for example as a co-molded part, thereby allowing the single unitary structure to accommodate syringes with distal ends of different dimensions and tolerances while still The compliant annular ring 222 of the inner body 220 may have a generally circular channel 244 to receive the proximal end 216b of the force member (e.g., a coil spring) 216. A circumferential step 246 (see, FIGS. 17 and 24) in the inner surface of the outer tube 212 is sized to receive and engage the distal end 216a of the force member 216. At least one collar pin 218 extends radially outwardly from the collar 214 and is slidably receivable in the track "T" in the outer tube 212. In embodiments in which the outer tube 212 has a plurality of tracks, the collar 214 may have a corresponding plurality of pins 218.

To mount the collar 214 to the barrel 202, the distal end 202a of the barrel 202 or hub 205 may be inserted into and through the proximal end 214b of the collar 214 and into and through the distal end 214a of the collar 214. As the hub 205 passes through the distal end 214a of the collar 214, the annular ring bore 224 in the compliant annular ring 222 expands until the distal end of the hub 205 passes therethrough. The annular ring bore 224 then returns to its initial state in which the distal end 214a of the collar 214 abuts the proximal surface 205b of the hub 205. In embodiments of the collar 214 in which the inner body 220 has the compliant side wall 226, the inner body 220 is fixedly attached to the distal end 202a of the barrel 202 by the compressive forces applied to the barrel 202 by the sidewall 226. In embodiments of the collar 214 in which the inner body 220 has radially inwardly biased flexible members 228 (see, FIGS. 22 and 23), the inner body 220 is fixedly attached to the distal end 202a of the barrel 202 by the flexible members 228.

Referring to FIGS. 17, 18 and 25-27, the cap 248 comprises an outer cylinder 250 having a closed distal end 250a with a generally hemispherical shape. An inner cylinder 252 within the outer cylinder 250 extends from the proximal end 250b of the outer cylinder 250 and forms an annular space 254 therebetween. The inner cylinder 252 is configured and dimensioned to receive therein the distal end 204a of the cannula shield 204 and to receive in the annular space 254 the distal end 212a of the outer tube 212. Diametrically opposed portions of the outer cylinder 250 form arms 256 which extend radially inwardly through cutouts 258 in the outer cylinder 250 and which have grips 260 which attach the cap 248 to the distal end 204a of the cannula shield 204 by applying a radially inwardly directed force thereto.

The cannula shield 204 (see, FIG. 18) has a tapered, generally cylindrical shape and is configured and sized to receive the cannula 203 therein and is removably positioned within the outer tube 212 and preferably within the biasing member 216. The cannula shield 204 has a closed distal end 204a within the cap 248 and to which the cap 248 is attached. The cannula shield 204 has a proximal end 204b which terminates in an annulus dimensioned to receive therein the hub 205 of the syringe barrel 202 and which removably engages the collar 214.

Figure 24:
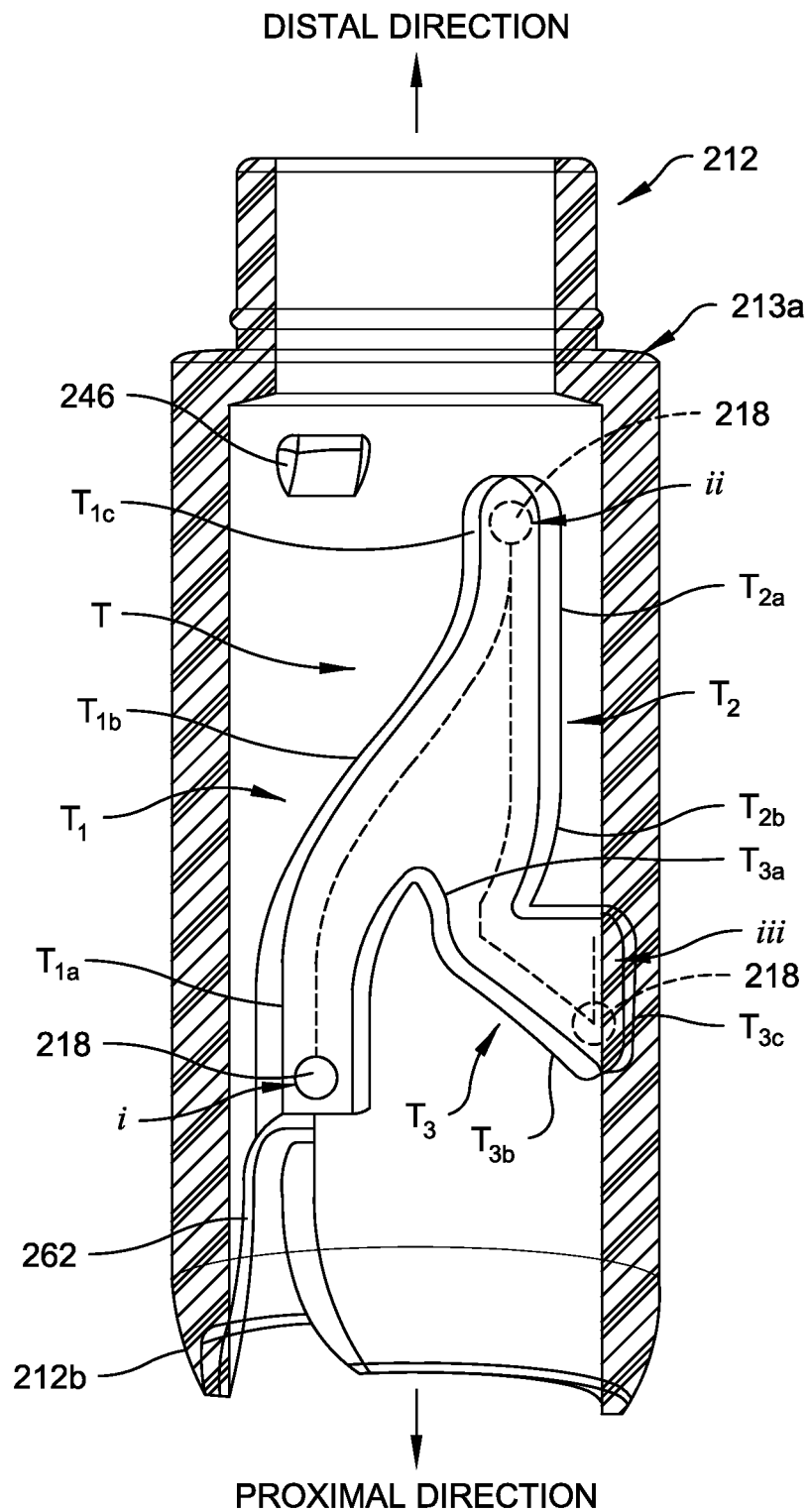
FIG. 24 is an enlarged elevation view of the left semi-cylindrical piece part of FIG. 18.

Referring to FIG. 24, the cannula 203 is in the cannula shield 204 and entirely within the outer tube 212 when the collar 214 is attached to the distal end 202a of the barrel 202 and the collar pin 218 is in a pre-injection position (i) in the track "T". The cannula 203 extends beyond the distal end 212a of the outer tube 212 when the collar 214 is attached to the distal end 202a of the barrel 202, the cannula shield 204 and cap 248 are removed from the outer tube 212 and the collar pin 218 is in a full-insertion position (ii) in the track "T". The cannula 203 is irreversibly retained entirely within the outer tube 212 when the collar 214 is attached to the distal end 202a of the barrel 202 and the collar pin 214 is in a locking position (iii) in the track "T".

Track T comprises: a first track segment $T_1$, a second track segment $T_2$ and a third track segment $T_3$. The first track segment $T_1$ extends between the pre-injection position (i) and the full-insertion position (ii). When an applied force greater than the biasing force moves the outer tube 212 in the proximal direction, the collar pin 218 moves from the pre-insertion position (i) to the full-insertion position (ii). The first track segment $T_1$ comprises an axially-extending first-track-segment first portion $T_{1a}$, a generally arcuate first-track-segment second portion $T_{1b}$ and a first-track-segment third portion $T_{1c}$.

The first-track-segment first portion $T_{1a}$ extends axially from the pre-injection position (i) toward the full-insertion position (ii) and constrains the collar pin 218 therein to move only in translation in the distal direction parallel to the longitudinal axis of the outer tube 212. The first-track-segment first portion $T_{1a}$ precedes and is contiguous with the first-track-segment second portion $T_{1b}$. The first-track-segment second portion $T_{1b}$ guides the collar pin 218 to slideably move simultaneously in translation and rotation only in the distal direction and in a first rotational direction about the longitudinal axis. The first-track-segment third portion $T_{1c}$ is contiguous with the first-track-segment second portion $T_{1b}$ and constrains the collar pin 218 therein to move only in translation in the distal direction to the full-insertion position (ii).

The second track segment $T_2$ extends from the full-insertion position (ii) to the beginning of the third track segment $T_3$. When the biasing force moves the outer tube 212 in the distal direction, the collar pin 218 moves away from the full-insertion position (ii) to the beginning of the third track segment $T_3$. The second track segment $T_2$ comprises a second-track-segment first portion $T_{2a}$ and a second-track-segment second portion $T_{2b}$.

The second-track-segment first portion $T_{2a}$ is contiguous with the first-track-segment third portion $T_{1c}$, extends proximally and axially from the full-injection position (ii) and constrains the collar pin 218 therein to move only in translation in the proximal direction. The second-track-segment first portion $T_{2a}$ precedes and is contiguous with the second-track-segment second portion $T_{2b}$. The second-track-segment second portion $T_{2b}$ guides the collar pin 218 to slideably move simultaneously in translation and rotation only in the proximal direction and a second rotational direction opposite the first rotational direction when the biasing force moves the outer tube in the distal direction.

The third track segment $T_3$ is contiguous with the second track segment $T_2$ and forms the locking position (iii) in which the collar pin 218 is irreversibly retained. The third track segment $T_3$ comprises an axially-extending third-track-segment first portion $T_{1a}$, a third-track-segment second portion $T_{3b}$ angled with respect to the longitudinal axis "A" of the outer tube 212 and a third-track-segment third portion $T_{3c}$.

The third-track-segment first portion $T_{1a}$ is contiguous with the second-track-segment second portion $T_{2b}$ and precedes and is contiguous with the third-track-segment second portion $T_{3b}$. The third-track-segment third portion $T_{3c}$ extends axially in the distal direction and circumferentially in the second rotational direction forming with the third-track-segment second portion $T_{3b}$ a lock (iii) preventing axial and circumferential movement of the collar pin 218 relative to the outer tube 212 as the force member 216 biases the collar pin 218 against movement in the distal direction while allowing rotational movement of the collar 214 in unison with the outer tube 212 relative to the hub 205 about which the collar 214 may freely rotate.

A staging track 262 in the inner surface of the outer tube 212 and extending from the proximal end 212b of the outer tube 212 to the first track segment $T_1$ in the inner wall of the outer tube 212 is provided to facilitate insertion of the collar pin 218 in the first track segment $T_1$.

To operate the injection device 201 filled with a medicant and having the safety device 200 attached thereto, the safety shield 4 is removed from the cannula 3 and set aside by grasping and moving the cap 248 distally along the longitudinal axis "A" until the proximal end of the cannula passes the distal end of the outer tube 212. Next, the injection site is located and the adjacent skin is sterilized and the distal end 212a of the outer tube 212 is positioned over the injection site and against the skin. At the initiation of an injection, the force applied by the skin to the outer tube 212 moves the collar pins 218 out of the pre-injection position (i) and along beginning of the first track segment T1. As the skin is being penetrated by the cannula 3, continued application of force by the skin to the outer tube 212 further moves the outer tube 212 in the proximal direction and the collar pins 218 in the distal direction along the first track segment T1 to the fully inserted position (ii). The outer tube 212 remains in the full-insertion position (ii) until withdrawal of the cannula 3 is initiated, typically after a full dose of the medicament is delivered.

As the cannula 3 is being withdrawn after the desired dose of medicament has been delivered, the force applied by the skin to the outer tube 212 decreases and the outer tube 212 moves in the distal direction relative to the collar 214 under the reactive force of the biasing member 216 compressed between the collar 214 and the outer tube 212. The collar pins 218 move in the proximal direction away from the full-insertion position (ii) to the beginning of the third track segment T3 which guides the collar pins 218 to the locked position (iii) at which the outer tube 212 is fully extended covering the cannula 3 in the entirety.

When the collar pins 218 are in the locked position (iii), the biasing member 216 prevents movement of the collar pins 218 in the distal direction while allowing rotational movement of the collar 214 in unison with the outer tube 212 relative to the hub 205 about which the collar 214 may freely rotate. The collar pins 218 are irreversibly retained in the locked position (iii) even if the force of the biasing member 216 is overcome as the circumferential extent of the third-track-segment third portion $T_{3c}$ is a structural stop preventing movement of the collar pins 218 in the distal direction.

Figure 28:
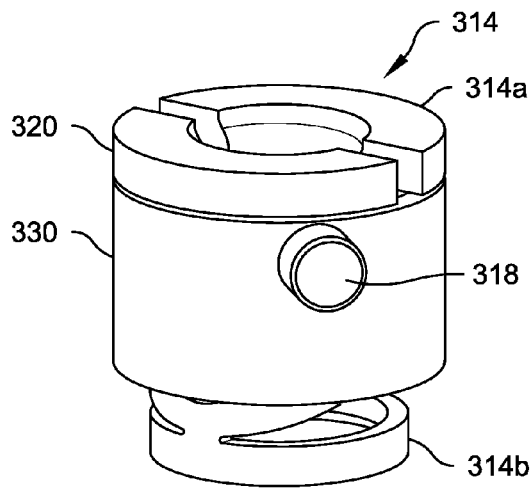
FIG. 28 is a top perspective view of another embodiment of a collar for the low radial-profile needle safety device in accordance with the present invention.
Figure 29:
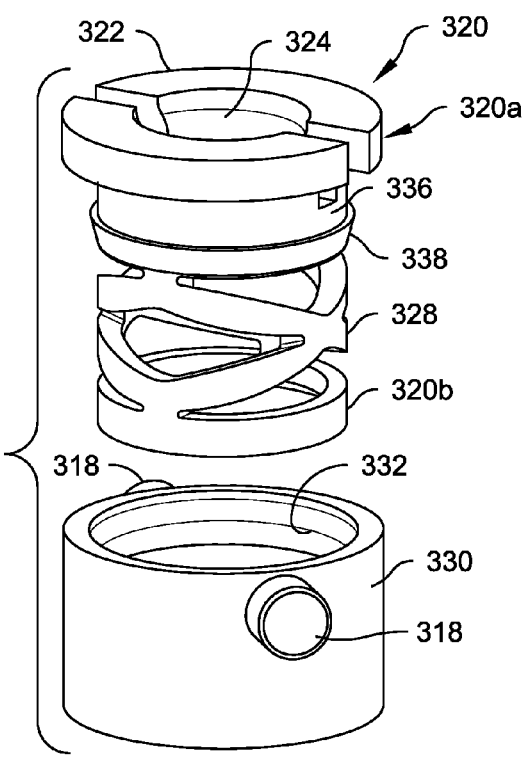
FIG. 29 is an exploded top perspective view of the collar of FIG. 28.
Figure 30:
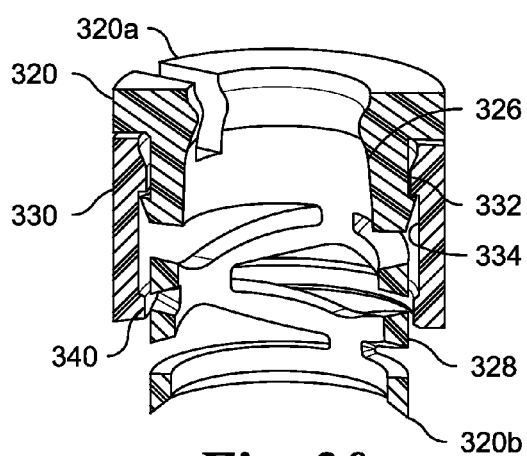
FIG. 30 is side cross section view of the collar of FIG. 28.

Referring to FIGS. 28-30, as an alternative to the collar assembly 214 disclosed above, the safety device 200 may comprise another preferred embodiment of a collar, generally designated 314, and hereinafter referred to as the collar 314 in accordance with the present invention. The collar 314 is a two-part assembly comprising at least a generally cylindrical inner body 320 fixedly attachable to the distal end 202a of the barrel 202 of the safety device 200 and a generally cylindrical outer body 330 which surrounds the inner body 320 and is rotatable relative thereto.

The cylindrical inner body 320 has a distal end 320a with a split annular ring 322 having an annular ring bore 324 able to pass therethrough the distal end 202a of the barrel 202. Further, a distal portion 326 of the cylindrical inner body 320 has an inner diameter less than the outer diameter of the distal end 202a of the barrel 202 such that the distal portion 326 may be fixedly attached to the distal end 202a of the barrel 202 by radially inwardly directed compressive forces applied to the distal end 202a of the barrel 202 by the distal portion 326 surrounding the distal end 202a of the barrel 202. A proximal portion 328 of the cylindrical inner body 320 is contiguous with the distal portion 326 and is compressible in a direction parallel to the longitudinal axis of the barrel 202. Preferably, the proximal portion 328 has a web-like structure. Preferably, but not necessarily, the longitudinal length of the cylindrical inner body 320 is greater than the length of the cylindrical outer body 330 and also greater than the distance between the shoulder 202c of the barrel 202 and the proximal surface 205b of the hub 205.

The cylindrical outer body 330 which surrounds the inner body 320 may be rotatably attached to the inner body 320 by at least one circumferential ring 332, extending radially inwardly from the inner surface 334 of the outer body 230 and received in an radially inwardly extending circumferential slot 336 in the outer surface 338 of the inner body 320. The circumferential ring 332 and slot 336 are sized such that the inner body 320 can be inserted in the outer body 330 by a snap fit while allowing rotation of the outer body 330 relative to the inner body 320. In some embodiments, a second circumferential ring 340 spaced from the at least one circumferential ring 332 may extend radially inwardly from the inner surface 334 of the outer body 230 to provide axial stability to the collar assembly 314.

At least one collar pin 318 extends radially outwardly form the collar 314 and is slidably receivable in the track "T" of the outer tube 212 of the safety device 200. In embodiments in which the outer tube 212 has a plurality of tracks, the collar 214 may have a corresponding plurality of pins 318.

To mount the collar 314 to the barrel 202, the distal end 202a of the barrel 202 or hub 205 is inserted into and through the proximal end 314b of the collar 314 and into and through the distal end 314a of the collar 314. As the hub 205 passes through the distal end 314a of the collar 314, the proximal end 320b of the cylindrical inner body 320 contacts the shoulder 202c of the barrel 202. Further passage of the hub 205 through the distal end 314a of the collar 314 compresses the proximal portion 328 of the cylindrical inner body 320. The annular ring bore 324 in the compliant annular ring 322 expands until the distal end of the hub 205 passes therethrough. Thereafter, the annular ring bore 324 returns to its initial state in which the distal end 314a of the collar 314 abuts and is held against the proximal surface 205b of the hub 205 by the biasing force of the compressed proximal portion 328 of the cylindrical inner body 320. Further, rotation of the cylindrical inner body 320 with respect to the distal end 202a of the barrel 202 is prevented by the compressive forces applied by the distal portion 326 of the cylindrical inner body 320 to the distal end 202a of the barrel 202.

Referring to FIGS. 31-33 in detail, where like numerals indicate like elements throughout, there is shown another preferred embodiment of a low radial profile needle safety device, generally designated 400, and hereinafter referred to as the "safety device" 400 in accordance with the present invention. The safety device 400 is substantially the same as the safety device 200 described above with the exception of the cap 428 for removing the cannula shield 404. For brevity, the following disclosure is directed to those features of the safety device 400 which differ from corresponding features in the safety device 200.

The safety device 400 is for an injection device, such as the injection device 201 disclosed above, having a generally cylindrical barrel 202 with a distal end having a hub 205 from which a cannula 203 extends. (See, FIG. 18) The safety device 400 has an outer tube 412 with a track formed in a inner surface 412$_i$ thereof substantially the same as the outer tube 212 and track "T" disclosed above. A collar 414 having a configuration substantially the same as any of the foregoing collars 14, 114, 214, 314 may be disposed within the outer tube 412. The collar 414 slideably engages the track "T" and attaches the safety device 400 to the injection device 201 in substantially the same manner as described above.

The safety device 400 has a cap 428 within which the outer tube 412 is disposed and by which the cap 428 is releasably retained. In a preferred embodiment, the cap 428 has diametrically-opposed, longitudinally-extending arms 430 received in a releasable friction fit in corresponding recesses 412a in the outer surface of the outer tube 412. A generally cylindrical shaped cannula shield 404 having a bore (not shown) configured to receive the cannula 203 is fixedly attached to the cap 428. Preferably, the distal end 404a of the cannula shield 404 has a radially outwardly extending disk-like flange 432 which is fixedly received in an annular bore 434 in the distal end 428a of the cap 428.

In use, the safety device 400 is mounted on the injection device 201 by inserting the cannula 203 in the bore of the cannula shield 404 and attaching the collar 414 to the distal end 202a of the barrel 202 by the application of a proximally-directed longitudinal force to the safety device 400. Prior to operating the injection device 201 for delivery of a medicament, the cap 428 with the cannula shield 404 attached thereto is removed by the application of a distally-directed longitudinal force to the cap 428.

The foregoing detailed description of the invention has been disclosed with reference to specific embodiments. However, the disclosure is not intended to be exhaustive or to limit the invention to the precise forms disclosed. Those skilled in the art will appreciate that changes could be made to the embodiments described above without departing from the broad inventive concept thereof. Therefore, the disclosure is intended to cover modifications within the spirit and scope of the present invention as defined by the appended claims.

We claim:

1. A needle safety device for an injection device having a generally cylindrical barrel with a distal end having a hub from which a cannula extends, the needle safety device comprising:
   an outer tube within which the barrel is slideably receivable, the outer tube having a distal end, a proximal end spaced from the distal and a longitudinal axis along which the outer tube is movable in a distal extended direction and in a proximal retracted direction opposite the distal extended direction;
   a track formed in an inner surface of the outer tube;
   a collar within the outer tube and movable relative thereto, the collar attachable to the distal end of the barrel and having a radially outwardly extending collar pin slideably engaging the track;
   a cannula shield within the outer tube, the cannula shield able to receive the cannula therein,
   a cap removably attached to the outer tube, the cannula shield fixedly attached to the cap, the cap having diametrically-opposed, longitudinally-extending arms received in a releasable friction fit in corresponding recesses in an outer surface of the outer tube and a distal end having an annular bore within which a radially outwardly extending disk-like flange of the cannula shield is fixedly received; and
   a biasing member within the outer tube applying in the distal direction a biasing force to the outer tube,
   wherein the cannula is in the cannula shield and entirely within the outer tube when the collar is attached to the distal end of the barrel and the collar pin is in a pre-injection position in the track spaced from the proximal end of the outer tube,
   wherein the cannula extends beyond the distal end of the outer tube when the collar is attached to the distal end of the barrel, the cannula shield and cap are removed from the outer tube and the collar pin is in a full-insertion position in the track proximal to the distal end of the outer tube; and
   wherein the cannula is irreversibly retained entirely within the outer tube when the collar is attached to the distal end of the barrel and the collar pin is in a locking position in the track between the pre-injection position and the full-insertion position.

2. The needle safety device according to claim 1, wherein the track comprises:
   a first track segment extending between the pre-injection position and the full-insertion position, a part of the first track segment guiding the collar pin to slideably move simultaneously in translation and rotation only in the distal direction and in a first rotational direction about the longitudinal axis, when an applied force greater than the biasing force moves the outer tube in the proximal direction;
   a second track segment contiguous with the full-insertion position of the first track segment, a part of the second track segment guiding the collar pin to slideably move simultaneously in translation and rotation only in the proximal direction and a second rotational direction opposite the first rotational direction when the biasing force moves the outer tube in the distal direction; and
   a third track segment contiguous with the second track segment, a part of the third track segment forming the locking position in which the collar pin is irreversibly retained.

3. The needle safety device according to claim 2 wherein the part of the first track segment is a generally arcuate first-track-segment second portion and the first track segment further comprises:
   an axially-extending first-track-segment first portion within which the collar pin is constrained to move only in translation in the distal direction parallel to the longitudinal axis of the outer tube, when an applied force greater than the biasing force moves the outer tube in proximal direction, the first-track-segment first portion preceding and contiguous with the first-track-segment second portion; and
   a first-track-segment third portion contiguous with the first-track-segment second portion and within which the collar pin is constrained to move only in translation in the distal direction, when an applied force greater than the biasing force moves the outer tube in proximal direction.

4. The needle safety device according to claim 2 wherein, the part of the second track segment is a generally arcuate second-track-segment second portion and the second track segment further comprises:
   an axially-extending second-track-segment first portion within which the collar pin is constrained to move only in translation in the proximal direction when the biasing force moves the outer tube in the distal direction, the second-track-segment first portion preceding and contiguous with the second-track-segment second portion.

5. The needle safety device according to claim 2, wherein the part of the third track segment is a third-track-segment second portion angled with respect to the longitudinal axis of the outer tube and the third track segment further comprises:

an axially-extending third-track-segment first portion within which the collar pin is constrained to move only in translation in the proximal direction when the biasing force moves the outer tube in the distal direction, the third-track-segment first portion preceding and contiguous with the third-track-segment second portion; and a third-track-segment third portion which is contiguous with the third-track-segment second portion and extends axially in the distal direction and circumferentially in the second rotational direction forming a lock preventing axial movement of the collar pin.

6. The needle safety device according to claim 1, wherein the biasing member surrounds the cannula shield.

7. The needle safety device according to claim 1, wherein the outer tube is disposed in the cap, and the cap is releasably retained by the outer tube.

* * * * *